US011383052B2

(12) United States Patent
Buchberger

(10) Patent No.: US 11,383,052 B2
(45) Date of Patent: Jul. 12, 2022

(54) ATOMIZER FOR VAPOR PROVISION DEVICE

(71) Applicant: NICOVENTURES TRADING LIMITED, London (GB)

(72) Inventor: Helmut Buchberger, London (GB)

(73) Assignee: Nicoventures Trading Limited, London (GB)

( * ) Notice: Subject to any disclaimer, the term of this patent is extended or adjusted under 35 U.S.C. 154(b) by 92 days.

(21) Appl. No.: 16/613,691

(22) PCT Filed: May 15, 2018

(86) PCT No.: PCT/GB2018/051303
§ 371 (c)(1),
(2) Date: Nov. 14, 2019

(87) PCT Pub. No.: WO2018/211252
PCT Pub. Date: Nov. 22, 2018

(65) Prior Publication Data
US 2021/0084983 A1    Mar. 25, 2021

(30) Foreign Application Priority Data

May 16, 2017  (GB) ..................... 1707805

(51) Int. Cl.
*A24F 40/485* (2020.01)
*A61M 15/06* (2006.01)
(Continued)

(52) U.S. Cl.
CPC ............ *A61M 15/06* (2013.01); *A24F 40/44* (2020.01); *A24F 40/46* (2020.01); *A24F 40/485* (2020.01); *A24F 40/60* (2020.01); *A24F 40/10* (2020.01)

(58) Field of Classification Search
CPC ........ A24F 40/485; A24F 40/46; A24F 40/44; A24F 40/60; A24F 40/10; A61M 15/06
(Continued)

(56) References Cited

U.S. PATENT DOCUMENTS

| 4,922,901 A | 5/1990 | Brooks |
| 8,393,331 B2 | 3/2013 | Hon |

(Continued)

FOREIGN PATENT DOCUMENTS

| CN | 102655773 A | 9/2012 |
| CN | 202722499 | 2/2013 |

(Continued)

OTHER PUBLICATIONS

International Preliminary Report on Patentability, Application No. PCT/GB2018/051303, dated Jul. 26, 2019, 10 pages.
(Continued)

*Primary Examiner* — Hae Moon Hyeon
(74) *Attorney, Agent, or Firm* — Patterson Thuente Pedersen, P.A.

(57) ABSTRACT

An atomizer for a vapor provision system includes a vaporization chamber having a volume; a vapor generating element disposed in the vaporization chamber for providing vapor into the vaporization chamber volume; at least one plenum chamber separated from the vaporization chamber; and an air flow path through the atomizer including a vapor collecting portion through the vaporization chamber smaller than the volume, along which air travels to collect vapor provided by the vapor generating element, and at least one transport portion through a plenum chamber, the or each transport portion delivering air to or collecting air from the vapor collection portion.

22 Claims, 12 Drawing Sheets

(51) Int. Cl.
  *A24F 40/46* (2020.01)
  *A24F 40/44* (2020.01)
  *A24F 40/60* (2020.01)
  *A24F 40/10* (2020.01)

(58) Field of Classification Search
  USPC .................................................. 131/328, 329
  See application file for complete search history.

(56) References Cited

U.S. PATENT DOCUMENTS

| | | | |
|---|---|---|---|
| 10,244,792 | B2* | 4/2019 | Rado ........................ A24F 40/44 |
| 2011/0094523 | A1* | 4/2011 | Thorens ............... H05B 1/0202 |
| | | | 131/194 |
| 2011/0290267 | A1 | 12/2011 | Yamada et al. |
| 2015/0090279 | A1 | 4/2015 | Chen |
| 2015/0114409 | A1* | 4/2015 | Brammer ................. A24F 40/50 |
| | | | 131/329 |
| 2016/0183596 | A1* | 6/2016 | Rado ........................ A24F 40/44 |
| | | | 392/395 |
| 2020/0205478 | A1* | 7/2020 | Dick ........................ A24F 40/46 |

FOREIGN PATENT DOCUMENTS

| | | |
|---|---|---|
| CN | 203662018 | 6/2014 |
| CN | 104661545 A | 5/2015 |
| CN | 105919164 | 6/2016 |
| CN | 105934171 A | 9/2016 |
| CN | 106659250 A | 5/2017 |
| DK | 2890258 T3 | 1/2017 |
| GB | 2529201 | 2/2016 |
| JP | 2015524259 A | 8/2015 |
| WO | WO 2014/012907 | 1/2014 |
| WO | WO15114325 | 8/2015 |
| WO | WO-2015114327 A1 | 8/2015 |
| WO | WO2015117704 | 8/2015 |
| WO | WO-2015117705 A2 | 8/2015 |
| WO | WO15177043 | 11/2015 |
| WO | WO16005601 | 1/2016 |
| WO | WO2016092259 | 6/2016 |

OTHER PUBLICATIONS

International Search Report and Written Opinion, Application No. PCT/GB2018/051303, dated Aug. 2, 2018, 13 pages.
Office Action for Canadian Application No. 3,063,305, dated Jan. 22, 2021, 5 pages.
Office Action for Japanese Application No. 2019-557636, dated Mar. 2, 2021, 7 pages.
Office Action dated May 20, 2020 for Russian Application No. 2019136668, 12 pages.
Search Report dated Aug. 18, 2021, for Chinese Patent Application No. 201880028928.7, 2 pages.
Application and Filing Receipt for U.S. Appl. No. 17/305,226, filled Jul. 1, 2021, Inventor: Buchberger et al.

* cited by examiner

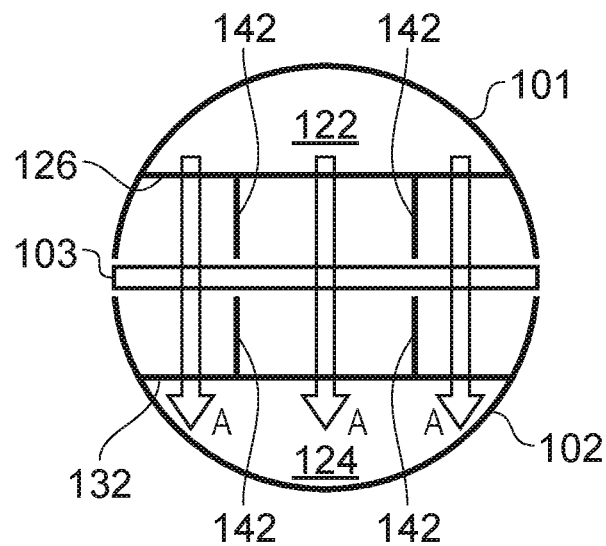
FIG. 15
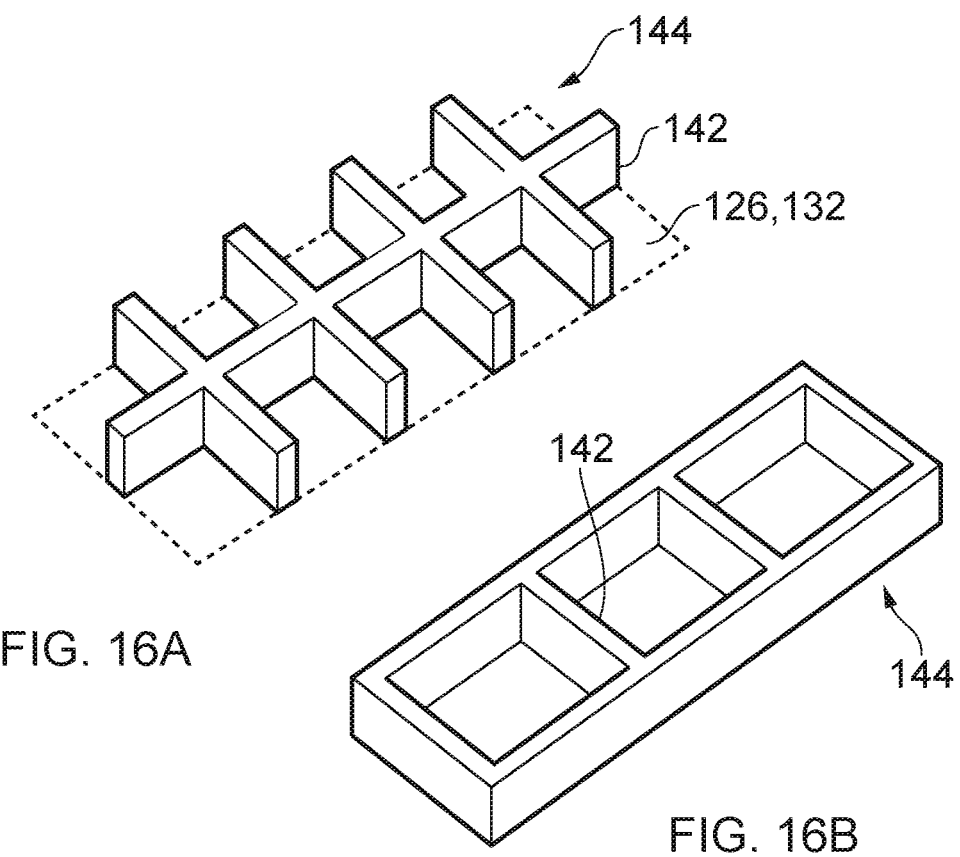
FIG. 16A
FIG. 16B

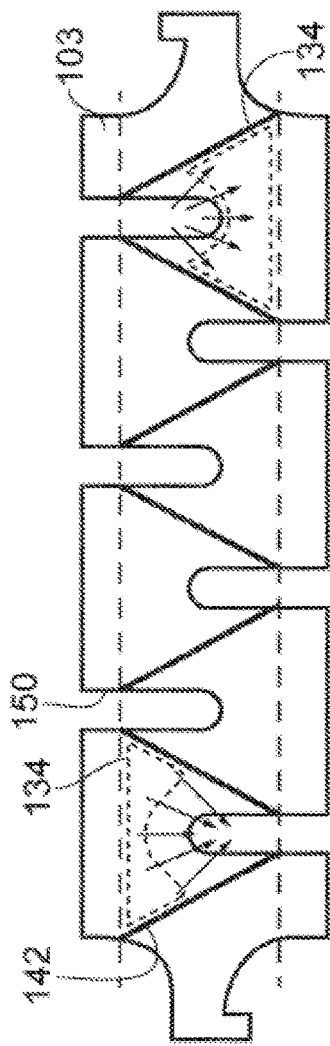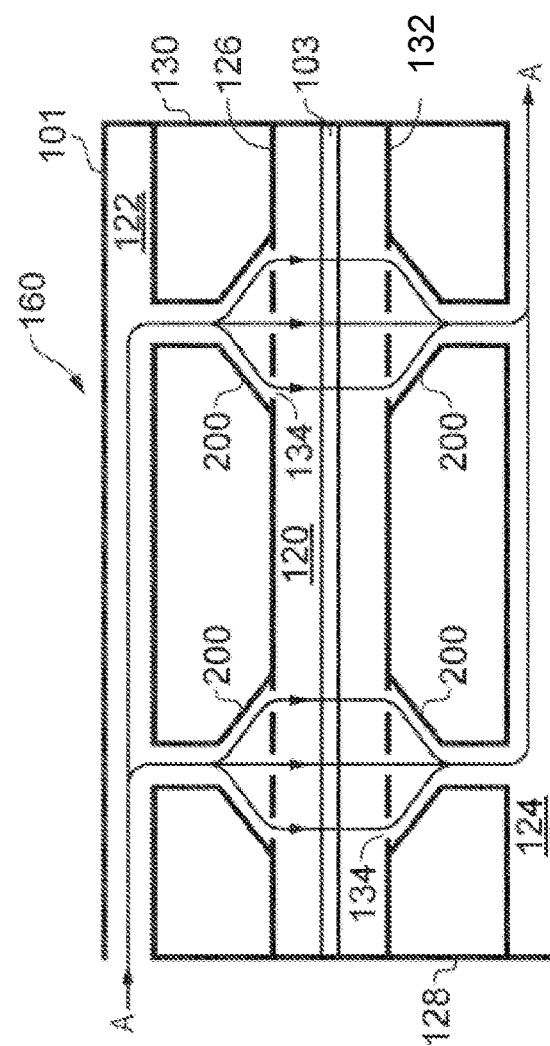

ATOMIZER FOR VAPOR PROVISION DEVICE

PRIORITY CLAIM

The present application is a National Phase entry of PCT Application No. PCT/GB2018/051303, filed May 15, 2018, which claims priority from GB Patent Application No. 1707805.6, filed May 16, 2017, each of which is hereby fully incorporated herein by reference.

TECHNICAL FIELD

The present disclosure relates to atomizers for use in vapor provision devices such as electronic vapor provision devices.

BACKGROUND

Vapor (aerosol) provision systems such as e-cigarettes generally comprise a reservoir of a source liquid containing a formulation, typically including nicotine, from which an aerosol is generated, such as through vaporization or other means. Thus an aerosol source for a vapor provision system may comprise a heating element or other vapor generating component coupled to a portion of the source liquid from the reservoir. In some systems, the heating element and reservoir are comprised within a first section or component which is connectable to a second section or component housing a battery to provide electrical power to the heating element. In use, a user inhales on the device to activate the heating element which vaporizes a small amount of the source liquid, which is thus converted to an aerosol for inhalation by the user.

In some devices, the vapor generating component is a heating element in the form of a wire coil. This is placed in contact with a wicking element that draws liquid from the reservoir by capillary action and delivers the liquid adjacent to the coil where it is heated and vaporized when an electrical current is passed through the coil. Air drawn into the device when a user inhales is carried over the heating element where it collects the vaporized source liquid to form an aerosol and carries this to an air outlet for consumption by the user. Various arrangements for positioning one or more coils with respect to the direction of air flow are known.

As an alternative, other devices employ a heating element in the form of a porous conductive sheet such as a metal mesh. The porosity allows the heating element to also perform a wicking function, so it draws liquid directly from the reservoir to be heated and vaporized when current is passed through the mesh. The sheet can be arranged to lie along the direction of air flow so that air can pass over both surfaces of the sheet to collect vaporized liquid.

Such arrangements can be very efficient at vapor generation and aerosol production. However, the extent of the sheet as compared to a coil means that flowing air tends to spend a relatively long time passing over the heater. This can allow the required aerosol droplets to increase to an undesirable size. Oversize droplets can be caught in the device and not reach the user, or can reduce the overall perceived quality of the aerosol as it is inhaled by the user.

Accordingly, approaches aimed at addressing this issue are of interest.

SUMMARY

According to a first aspect of certain embodiments described herein, there is provided an atomizer for a vapor provision system comprising: a vaporization chamber having a volume; a vapor generating element disposed in the vaporization chamber for providing vapor into the vaporization chamber volume; at least one plenum chamber separated from the vaporization chamber; and an air flow path through the atomizer comprising: a vapor collecting portion through the vaporization chamber smaller than said volume, along which air travels to collect vapor provided by the vapor generating element; and at least one transport portion through a plenum chamber, the or each transport portion delivering air to or collecting air from the vapor collection portion.

According to a second aspect of certain embodiments described herein, there is provided a vapor provision system, an aerosol generating component for a vapor provision system, or an aerosol source for an aerosol generating component for a vapor provision system or for a vapor provision system, comprising an atomizer according to the first aspect.

According to a third aspect of certain embodiments described herein, there is provided An atomizer for a vapor provision system comprising: a vaporization chamber; a planar vapor generating element disposed in the vaporization chamber and comprising a longitudinally extending porous sheet having a first surface and an opposite second surface; at least one plenum chamber separated from the vaporization chamber and transversely spaced from a surface of the vapor generating element; and an air flow path through the atomizer comprising: a vapor collecting portion through the vaporization chamber in which air travels transversely through the vapor generating element from the first surface to the second surface; and at least one transport portion through a plenum chamber in which air travels longitudinally, the or each transport portion delivering air to or collecting air from the vapor collection portion.

These and further aspects of certain embodiments are set out in the appended independent and dependent claims. It will be appreciated that features of the dependent claims may be combined with each other and features of the independent claims in combinations other than those explicitly set out in the claims. Furthermore, the approach described herein is not restricted to specific embodiments such as set out below, but includes and contemplates any appropriate combinations of features presented herein. For example, an atomizer or a vapor provision device or a component therefor including an atomizer may be provided in accordance with approaches described herein which includes any one or more of the various features described below as appropriate.

BRIEF DESCRIPTION OF THE DRAWINGS

Various embodiments will now be described in detail by way of example only with reference to the accompanying drawings in which:

FIG. 15 shows a schematic transverse cross-sectional view through an example atomizer with plenum chambers and partition walls.

FIGS. 16A and 16B show perspective views of example inserts for providing an atomizer with partition walls and separating walls to create plenum chambers.

FIGS. 17 to 21 are plan views of example vapor generating elements for use in an atomizer according to examples disclosed herein.

FIG. 22 is a schematic longitudinal cross-sectional view through an example atomizer configured for non-longitudinal airflow in a transport portion of the airflow path.

DETAILED DESCRIPTION

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

As described above, the present disclosure relates to (but is not limited to) electronic aerosol or vapor provision systems, such as e-cigarettes. Throughout the following description the terms "e-cigarette" and "electronic cigarette" may sometimes be used; however, it will be appreciated these terms may be used interchangeably with aerosol (vapor) provision system or device. Similarly, "aerosol" may be used interchangeably with "vapor", particularly as regards the final consumable output of a device, carried on an airstream for inhalation by a user.

Figure 1:
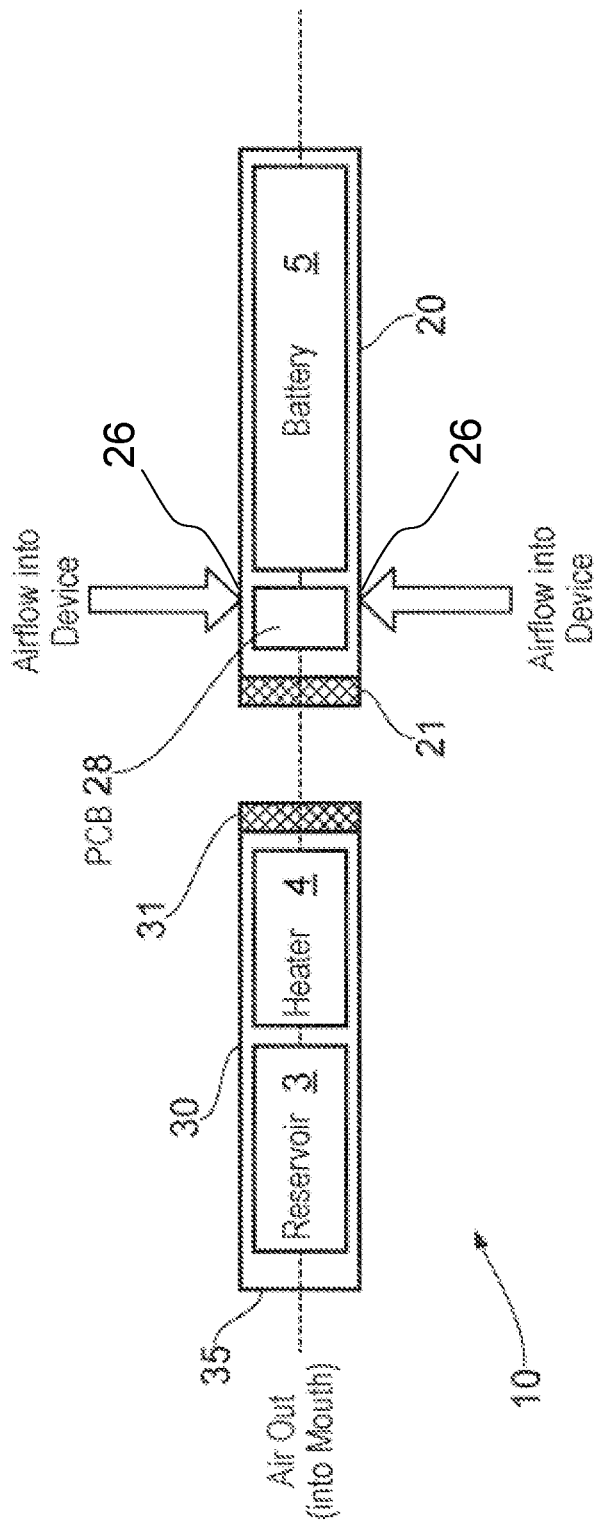
FIG. 1 shows a simplified schematic cross-sectional view of an example electronic cigarette or vapor provision system.

FIG. 1 is a highly schematic diagram (not to scale) of an example aerosol/vapor provision system such as an e-cigarette 10. The e-cigarette 10 has a generally cylindrical shape, extending along a longitudinal axis indicated by a dashed line, and comprises two main components, namely a control or power component or section 20 and a cartridge assembly or section 30 (sometimes referred to as a cartomizer, or clearomizer) that operates as a vapor generating component.

The cartridge assembly 30 includes a reservoir 3 containing a source liquid comprising a liquid formulation from which an aerosol is to be generated, for example containing nicotine. As an example, the source liquid may comprise around 1 to 3% nicotine and 50% glycerol, with the remainder comprising roughly equal measures of water and propylene glycol, and possibly also comprising other components, such as flavorings. The reservoir 3 has the form of a storage tank, being a container or receptacle in which source liquid can be stored such that the liquid is free to move and flow within the confines of the tank. Alternatively, the reservoir 3 may contain a quantity of absorbent material such as cotton wadding or glass fiber which holds the source liquid within a porous structure. The reservoir 3 may be sealed after filling during manufacture so as to be disposable after the source liquid is consumed, or may have an inlet port or other opening through which new source liquid can be added. The cartridge assembly 30 also comprises an electrical vapor generating element 4 located externally of the reservoir 3 for generating the aerosol by vaporization of the source liquid. In many devices, the vapor generating element may be a heating element (heater) which is heated by the passage of electrical current (via resistive or inductive heating) to raise the temperature of the source liquid until it evaporates. Alternatively, the vapor generating element may vibrate at a high frequency (for example an ultrasonic frequency), using the piezoelectric effect, for example, to generate vapor from the source liquid. A liquid conduit arrangement such as a wick or other porous element (not shown) may be provided to deliver source liquid from the reservoir 3 to the vapor generating element 4. The wick has one or more parts located inside the reservoir 3 so as to be able to absorb source liquid and transfer it by wicking or capillary action to other parts of the wick that are in contact with the vapor generating element 4. This liquid is thereby vaporized, to be replaced by new source liquid transferred to the vapor generating element 4 by the wick.

A heater and wick combination, or other arrangement of parts that perform the same functions, is sometimes referred to as an atomizer or atomizer assembly, and the reservoir with its source liquid plus the atomizer may be collectively referred to as an aerosol source. Various designs are possible, in which the parts may be differently arranged compared to the highly schematic representation of FIG. 1. For example, the wick may be an entirely separate element from the vapor generating element, or the vapor generating element may be configured to be porous and able to perform the wicking function directly (a metallic mesh, for example). Arrangements of this latter type, where the functions of the vapor generation and wicking are combined in a single element, are discussed further below. In some cases, the conduit for delivering liquid for vapor generation may be formed at least in part from one or more slots, tubes or channels between the reservoir and the vapor generating element which are narrow enough to support capillary action to draw source liquid out of the reservoir and deliver it for vaporization. In general, an atomizer can be considered to be a vapor generating or vaporizing element able to generate vapor from source liquid delivered to it, and a liquid conduit (pathway) able to deliver or transport liquid from a reservoir or similar liquid store to the vapor generator such as by a capillary force.

Typically, the atomizer is located within a volume or chamber that forms part of an airflow channel through the electronic cigarette. Vapor produced by the atomizer is driven off into this volume, and as air passes through the volume, flowing over and around the vapor generating element, it collects the vapor, forming the required aerosol. The volume can be designated as a vaporization chamber.

Returning to FIG. 1, the cartridge assembly 30 also includes a mouthpiece 35 having an opening or air outlet through which a user may inhale the aerosol generated by the vapor generating element 4, and delivered through the airflow channel.

The power component 20 includes a cell or battery 5 (referred to herein after as a battery, and which may be re-chargeable) to provide power for electrical components of the e-cigarette 10, in particular the vapor generating element 4. Additionally, there is a printed circuit board (PCB) 28 and/or other electronics or circuitry for generally controlling the e-cigarette. The control electronics/circuitry connect the vapor generating element 4 to the battery 5 when vapor is required, for example in response to a signal from an air pressure sensor or air flow sensor (not shown) that detects an inhalation on the system 10 during which air enters through one or more air inlets 26 in the wall of the power component 20 to flow along the airflow channel. When the vapor generating element 4 receives power from the battery 5, the vapor generating element 4 vaporizes source liquid delivered from the reservoir 3 to generate the aerosol, and this is then inhaled by a user through the opening in the mouthpiece 35. The aerosol is carried from the aerosol source to the mouthpiece 35 along the airflow channel (not shown) that connects the air inlet 26 to the aerosol source to the air outlet when a user inhales on the mouthpiece 35. An airflow path through the electronic cigarette is hence defined, between the air inlet(s) (which may or may not be in the power component) to the atomizer and on to the air outlet at the mouthpiece. In use, the air flow direction along this airflow path is from the air inlet to the air outlet, so that the atomizer can be described as lying downstream of the air inlet and upstream of the air outlet.

In this particular example, the power section 20 and the cartridge assembly 30 are separate parts detachable from one another by separation in a direction parallel to the longitudinal axis, as indicated by the solid arrows in FIG. 1. The sections 20, 30 are joined together when the device 10 is in use by cooperating engagement elements 21, 31 (for example, a screw or bayonet fitting) which provide mechanical and electrical connectivity between the power section 20 and the cartridge assembly 30. This is merely an example arrangement, however, and the various components may be differently distributed between the power section 20 and the cartridge assembly or section 30, and other components and elements may be included. The two sections may connect together end-to-end in a longitudinal configuration as in FIG. 1, or in a different configuration such as a parallel, side-by-side arrangement. The system may or may not be generally cylindrical and/or have a generally longitudinal shape. Either or both sections may be intended to be disposed of and replaced when exhausted (the reservoir is empty or the battery is flat, for example), or be intended for multiple uses enabled by actions such as refilling the reservoir, recharging the battery, or replacing the atomizer. Alternatively, the e-cigarette 10 may be a unitary device (disposable or refillable/rechargeable) that cannot be separated into two or more parts, in which case all components are comprised within a single body or housing. Embodiments and examples of the present disclosure are applicable to any of these configurations and other configurations of which the skilled person will be aware.

Herein, the terms "heater" and "heating element" may be used, but unless the context specifically indicates a heating operation, these terms should be understood to refer to vapor generating elements in general and including other types of vapor generating elements such as those which operate by vibration.

As mentioned, a type of vapor generating element such as a heating element that may be utilized in an atomizing portion of an electronic cigarette (a part configured to generate vapor from a source liquid) combines the functions of heating and liquid delivery, by being both electrically conductive (resistive) and porous. An example of a suitable material for this is an electrically conductive material such as a metal or metal alloy formed into a fine mesh, web, grill or similar configuration having a sheet format, i.e. a planar shape with a thickness many times smaller than its length or breadth. The mesh may be formed from metal wires or fibers which are woven together, or alternatively aggregated into a non-woven structure. For example, fibers may be aggregated by sintering, in which heat and/or pressure are applied to a collection of metal fibers to compact them into a single porous mass.

These structures can give appropriately sized voids and interstices between the metal fibers to provide a capillary force for wicking liquid. Also, the metal is electrically conductive and therefore suitable for resistive heating, whereby electrical current flowing through a material with electrical resistance generates heat. Structures of this type are not limited to metals, however; other conductive materials may be formed into fibers and made into mesh, grill or web structures. Examples include ceramic materials, which may or may not be doped with substances intended to tailor the physical properties of the mesh.

A planar sheet-like porous heating element of this kind can be arranged within an electronic cigarette such that it lies within the vaporization chamber part of an airflow channel in an orientation parallel to the airflow direction. Air can thence flow over both sides of the heating element, and gather vapor. Aerosol generation is thereby made very effective. The reservoir of source liquid can have an annular shape, surrounding the vaporization chamber and divided therefrom by a tubular wall. The heating element extends across the width of the vaporization chamber and is supported in place by its edges passing through the dividing wall or resting in gaps in the wall. In this way, edge portions of the heating element are positioned in contact with the reservoir interior and can collect liquid therefrom by capillary action. This liquid is drawn into more central portions of the heating element. Electrical connections are provided on the heating element which enable the passage of electrical current, producing the required heating to vaporize the liquid held in the porous structure of the heating element. Vapor is delivered into the vaporization chamber for collection by the flow of air along the airflow channel. Alternatively, the heating current may comprise eddy currents generated by electromagnetic induction, requiring an electromagnet to produce a rapidly alternating magnetic field penetrating the vapor producing element.

Figure 2:
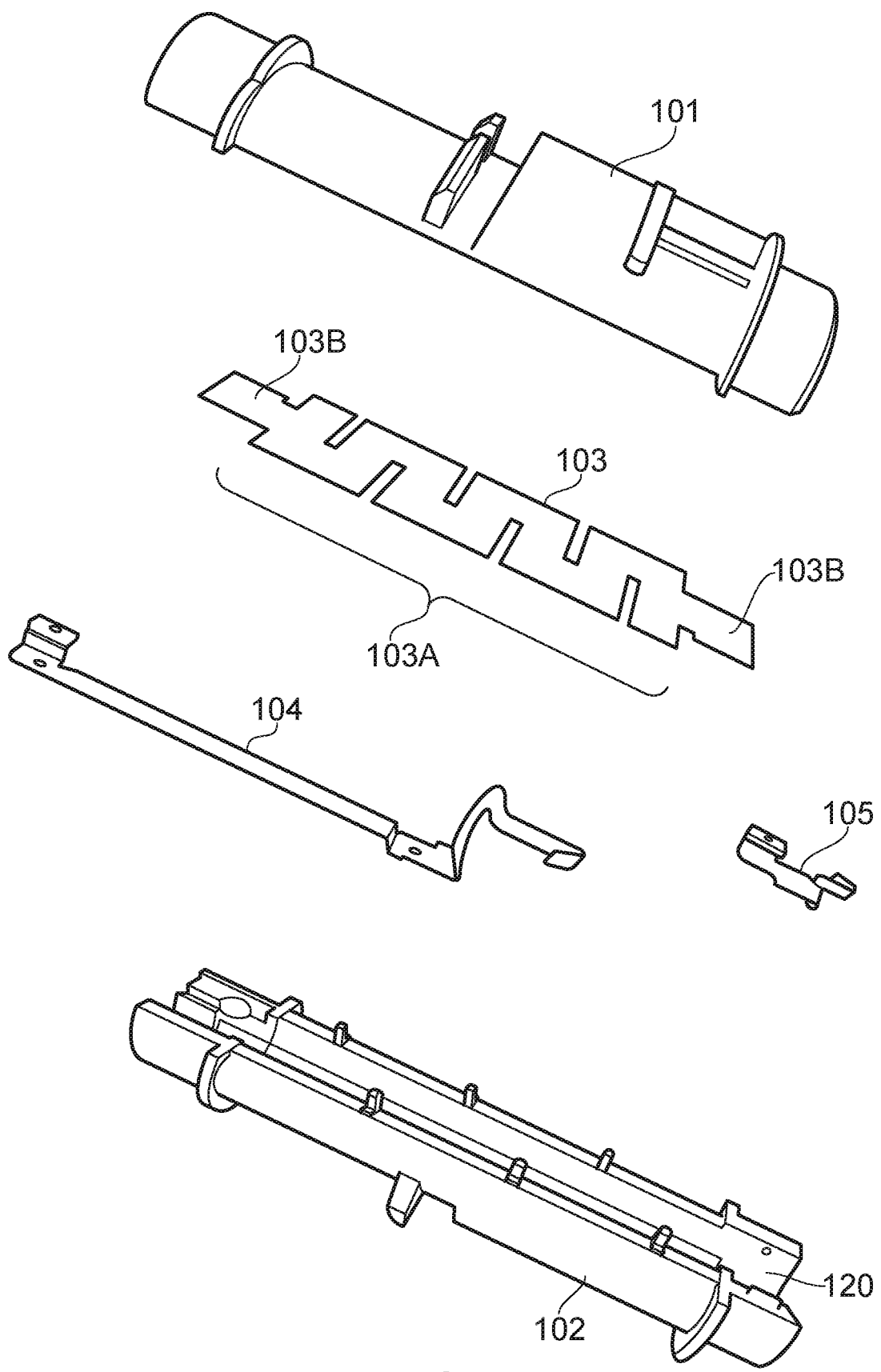
FIG. 2 shows an exploded perspective view of parts of an example atomizer for use in an electronic cigarette.
Figure 3:
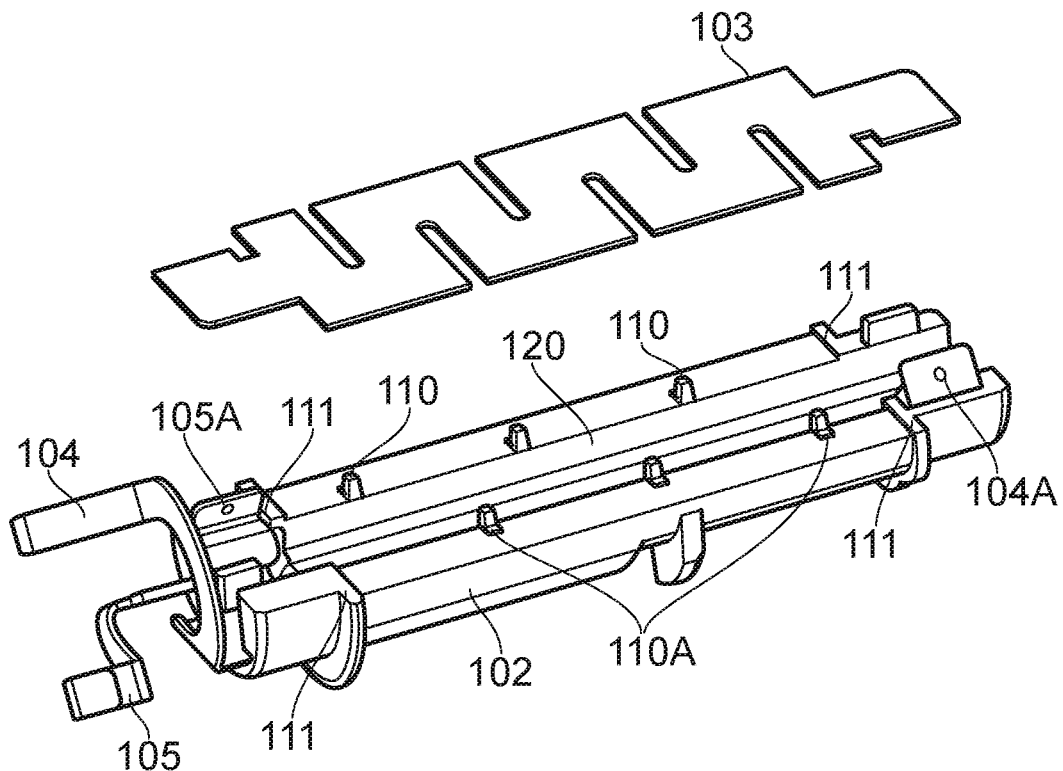
FIGS. 3 to 6 shows perspective views of the atomizer parts shown in FIG. 2 in successive stages of assembly into a completed atomizer.

FIG. 2 shows an exploded perspective view of various components of an example atomizer of this format. FIGS. 3 to 6 show perspective views of the components represented in FIG. 2 at different stages of assembly.

The atomizer 160 comprises a first carrier component (first part) 101 and a second carrier component (second part) 102. These two components 101, 102 play a role in supporting a planar heating element 103, and in this regard may sometimes be referred to as providing a heating element cradle. Thus, the first and second components 101, 102 represented in FIG. 2 may for convenience, and having regard to the orientation represented in the figures, also be referred to as an upper cradle 101 and a lower cradle 102. The atomizer 160 further comprises the heating element 103, a first electrical contact element 104 for connecting to a first end of the heating element 103 and a second electrical contact element 105 for connecting to a second end of the heating element 103.

The upper and lower cradle components 101, 102 may be molded from a plastics material having a high glass fiber content (e.g. 50%) to provide improved rigidity and resistance to high temperatures, for example temperatures around 230 degrees centigrade. The respective upper and lower cradle components are broadly speaking of a generally semi-circular cross-section (although with variations in size and shape along their lengths as discussed further below). Each cradle component is provided with a recess 120 (only visible for lower cradle component 102 in FIG. 2) running along its length on what would otherwise be their flattest faces so that when the two cradle components are brought together to sandwich the heating element 103 as discussed further below they form a cradle having a generally tubular configuration with an airflow path (defined by the respective recesses 120) running down the interior of the tube and in which the heating element 103 is disposed. The airflow path formed by the two recessed 120 comprises the vaporization chamber of the atomizer 160.

The first and second electrical contact elements 104, 105 may be formed of a sheet metal material, for example comprising copper strips formed into an appropriate shape having regard to the shape and configuration of the other elements of the apparatus in accordance with conventional manufacturing techniques, or may comprise conventional flexible wiring.

The planar heating element 103 is formed from a sintered metal fiber material and is generally in the form of a sheet. However, it will be appreciated that other porous conducting materials may equally be used. In this particular example the heating element 103 comprises a main portion 103A with electrical contact extensions 103B at each end for connecting to the respective electrical contact elements 104, 105. In this example, the main portion 103A of the heating element is generally rectangular with a longitudinal dimension (i.e. in a direction running between the electrical contact extensions 103B) of around 20 mm, and a width of around 8 mm. The longitudinal dimension corresponds to the direction of airflow through the vaporization chamber (note that in other examples, the longitudinal dimension need not be the longest dimension of the heating element). The thickness of the sheet comprising the heating element 103 in this example is around 0.15 mm. As can be seen in FIG. 2, the generally-rectangular main portion 103A of the heating element 103 has a plurality of openings in the form of slots extending inwardly from each of the longer sides (sides parallel to the longitudinal direction). The slots extend inwardly by around 4.8 mm and have a width of around 0.6 mm. The slots extending inwardly are separated from one another by around 5.4 mm on each side of the heating element with the slots extending inwardly from the opposing sides being offset from one another by around half this spacing. In other words, the slots are alternately positioned along the longitudinal sides. A consequence of this arrangement of slots in the heating element is that current flow along the heating element is in effect forced to follow a meandering path which results in a concentration of current, and hence electrical power, around the ends of the slots. The different current/power densities at different locations on the heating element give areas of relatively high current density that become hotter than areas of relatively low current density. This provides the heating element with a range of different temperatures and increases temperature gradients, which can be desirable in the context of aerosol provision systems. This is because different components of a source liquid may aerosolize aerosolize/vaporize at different temperatures, so providing a heating element with a range of temperatures can help simultaneously aerosolize a range of different components in the source liquid.

A process of assembling the components represented in FIG. 2 to provide an atomizer 160 such as for use in a cartridge assembly 30 of an electronic cigarette 10 in is now described with reference to FIGS. 3 to 6.

As can be seen in FIG. 3, the first and second electrical contact elements 104, 105 have been mounted to the lower cradle component 102 and the heating element 103 is represented above the lower cradle component 102 ready to be put in place. The second electrical contact element 105 is mounted at a second end of the lower cradle component 102 (the leftmost end for the orientation in FIG. 3). One end of the second electrical contact element 105 provides a second electrical contact element clamp portion 105A for receiving one of the electrical contact extensions 103B of the heating element 103 while the other end of the second electrical contact element 105 extends away from the lower cradle component 102 as shown in the figure. The first electrical contact element 104 is mounted so as to run along the length of the lower cradle component 102 adjacent a wall of the recess 120. One end of the first electrical contact element 104 extends away from the second end of the lower cradle component 102 as schematically represented in the figure. The other end of the first electrical contact element 104 provides a first electrical contact element clamp portion 105A arranged at a first end of the lower cradle component 102 (rightmost end in FIG. 3) for receiving the other of the electrical contact extensions 103B of the heating element 103.

An upper surface of the lower cradle component 102 comprises a plurality of locating pegs 110 which align with the slots in the heating element discussed above and corresponding locating holes in the upper cradle 101 (not shown in the figures). These locating pegs are for helping to align the upper cradle 101 with the lower cradle 102, and for helping to align the heating element 103 relative to the upper and lower cradles 102 when assembled.

FIG. 4 shows the heating element 103 mounted to the lower cradle 102 containing the first and second electrical contact elements 104, 105. The heating element 103 is mounted to the lower cradle simply by being placed on the upper surface of the lower cradle with the locating pegs 110 aligned with the slots of the heating element 103. Slightly raised portions of the upper surface of the lower cradle element 102 provide locating walls 111 in the vicinity of the electrical contact extensions 103B at each end of the heating element 103 to further help align the heating element. In this example, the locating walls are separated by slightly more than the size of the heating element and the locating pegs are slightly smaller than the size of the slots so the heating element is overall free to move slightly in the horizontal plane, for example by around 0.1 mm. This is to allow for thermal expansion and contraction when the heating element is in use to help avoid buckling. The first and second electrical contact element clamping portions 104A, 105A are bent down so as to clamp around respective ones of the electrical contact extensions 103B at each end of the heating element 103, thus providing an electrical connection between the portions of the electrical contact elements 104, 105 extending away from the lower cradle component 102 and the ends of the heating element 103. In this example the electrical connections between the electrical contact elements 104, 105 and the heating element 103 rely solely on physical contact, but in other implementations other techniques may be used, for example welding or soldering.

Figure 4:
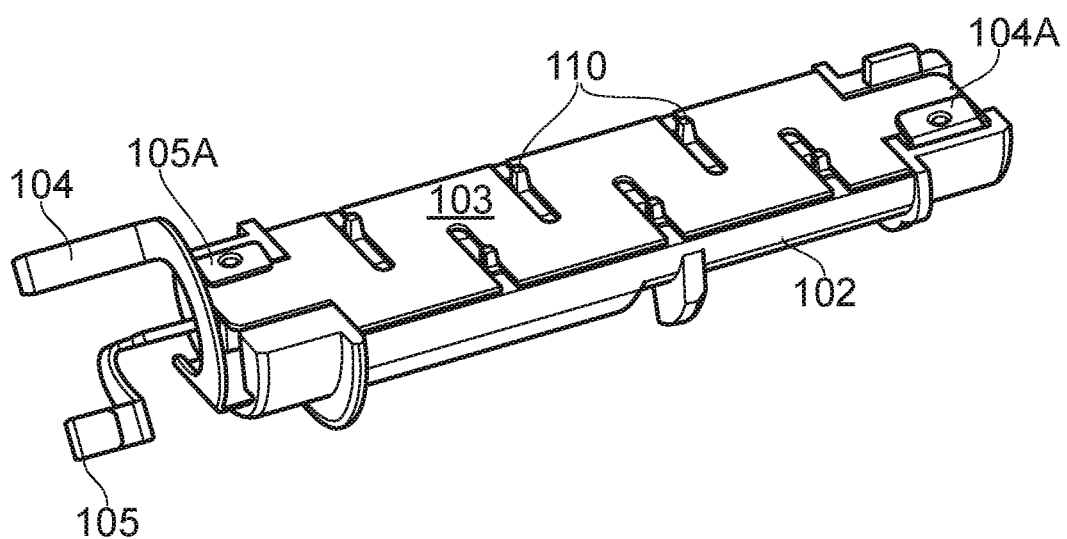
Figure 5:
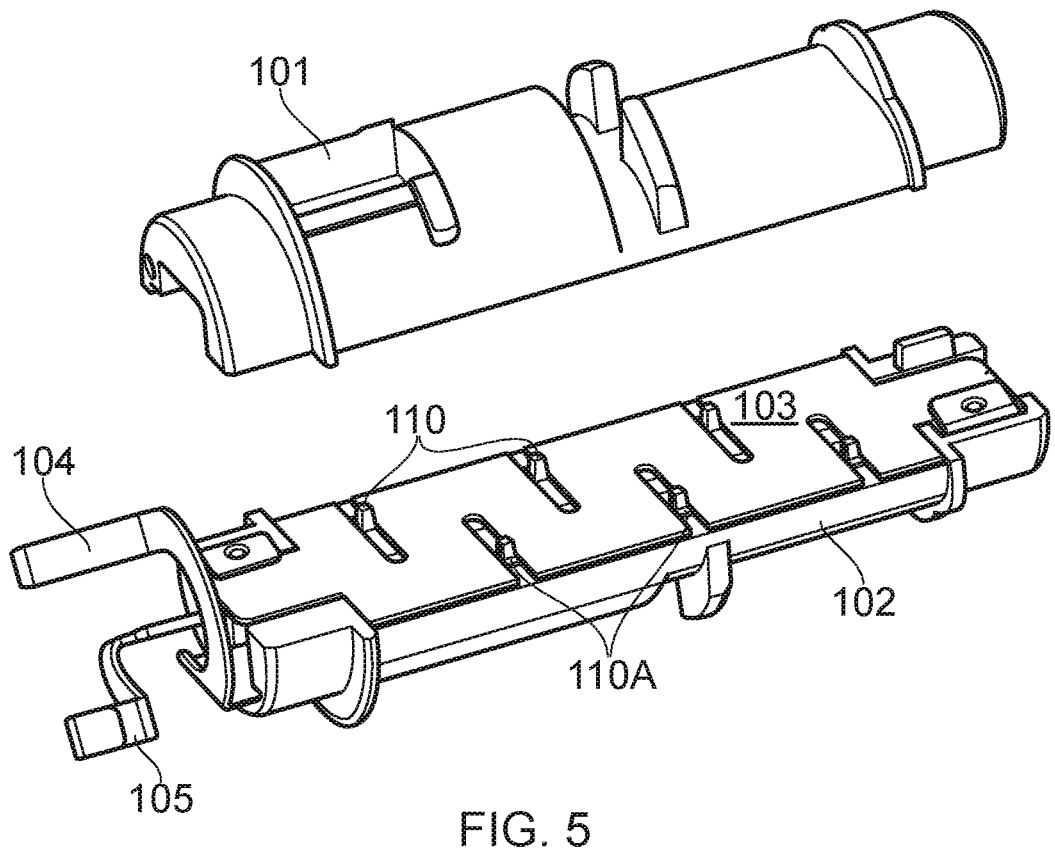

FIG. 5 shows the combined lower cradle component 102, first and second electrical contact elements 104, 105 and the heating element 103 as represented in FIG. 4, but with the other cradle component 101 shown ready to be mounted to the lower cradle component.

Figure 6:
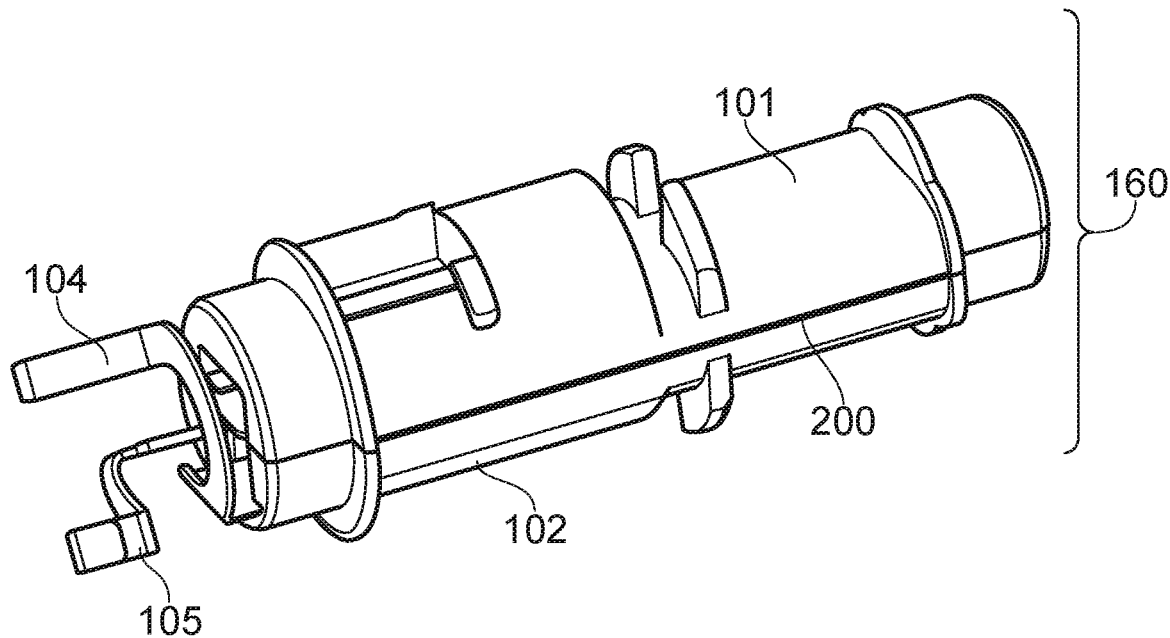

FIG. 6 schematically shows the upper cradle component 101 mounted to the lower cradle component 102 (and other elements represented in FIG. 4) to provide an assembled atomizer 160. The upper cradle component 101 is mounted to the lower cradle component 102 by simply placing them together with the locating pegs 110 of the lower cradle component aligned with corresponding locating holes (not shown) in the upper cradle component 101. As can be seen in FIGS. 4 and 5, the locating pegs 110 are each provided with a shoulder 110A. The shoulders 110A have a height above the upper surface of the lower cradle component 102 that matches the height of the locating walls 111 but is slightly larger than the thickness of the heating element 103. The shoulders 110A are sized and arranged so as to fall within the slots of the heating element. However, the corresponding locating holes in the upper cradle are sized only to receive the locating pegs, and not their shoulders. Thus, when the upper cradle component 101 is mounted to the lower cradle component 102 they are separated by a gap 200 corresponding to the height of the shoulders 110A and the locating walls 111. The gap is greater than the thickness of the heating element, so the heating element is loosely sandwiched between the upper and lower cradle components, rather than being fixedly clamped in place. As noted above, this loose mounting of the heating element is to allow for thermal expansion and contraction of the heating element during use.

Thus the assembled atomizer 160 is generally tubular with a central passageway forming a vaporization chamber defined by the respective recesses 120 in the upper and lower carrier components, providing an airflow path through the atomizer that will connect to an air inlet and an air outlet in a complete electronic cigarette. In use, the atomizer 160 is annularly surrounded by the reservoir of source liquid. The gap 200 is in fluid communication with the reservoir and hence provides capillary channels which extend along both sides of the heating element 103 and through which source liquid may be drawn from the reservoir to the heating element where it enters the pores of the heating element for vaporization to generate a vapor in the vaporization chamber 120 during use. The passing air collects the vapor to generate an aerosol to be drawn out of the vaporization chamber and along a further part of the airflow path through the electronic cigarette 10 to exit through the air outlet as a user inhales on the electronic cigarette 10.

When installed in an electronic cigarette, an atomizer may be arranged such that the longitudinal dimension of the heating element, corresponding to the direction of airflow through the atomizer from the upstream to downstream ends, is aligned parallel to the longitudinal axis of the electronic cigarette for an end-to-end device such as the FIG. 1 example, or at least the longitudinal axis of the cartridge component in a side-by-side device having a power component arranged to the side of a cartridge component. This is not compulsory, however, and in the current description, the term "longitudinal" is intended to refer to the dimensions and orientation of the atomizer, in particular the dimension of the heating element along the airflow path from an atomizer inlet at the upstream end of the atomizer, and through the vaporization chamber to the atomizer outlet at the downstream end of the atomizer.

Figure 7:
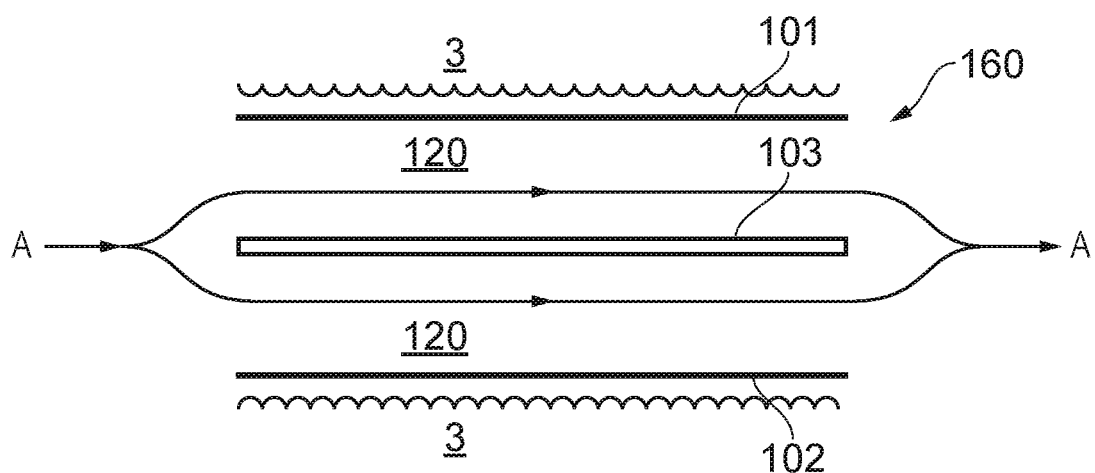
FIG. 7 shows a schematic longitudinal cross-sectional view through an example atomizer.
Figure 8:
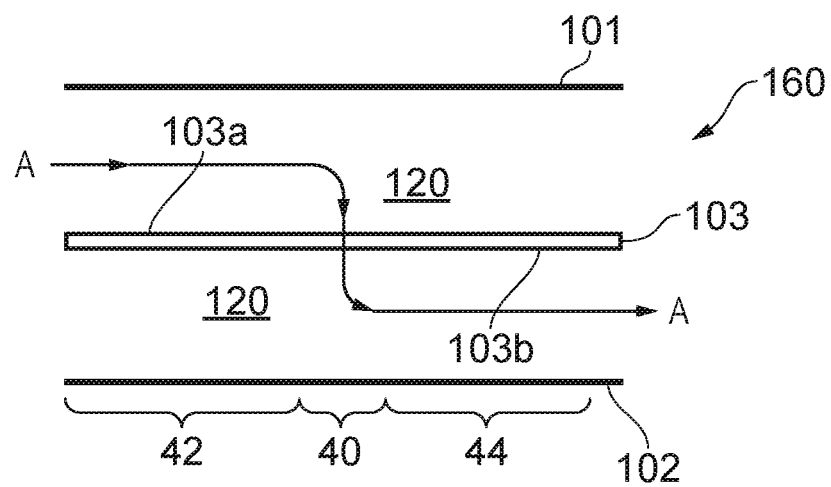
FIG. 8 shows a schematic longitudinal cross-sectional view through an example atomizer having a modified airflow path.

FIG. 7 shows a highly simplified longitudinal cross-sectional side view of the example atomizer 160 in use, where the section is orthogonal to the plane of the heating element 103. The upper and lower cradle components 101 and 102 (or similar housing to form the vaporization chamber and support the heater) form outer walls which divide the interior of the atomizer 160 from the surrounding reservoir 3. The interior forms the vaporization chamber 120. The heating element 103, which is shown edge-on, extends longitudinally through the vaporization chamber 120, and generates vapor into the vaporization chamber as discussed. An upstream end (shown left) of the vaporization chamber 120 connects with an upstream part of the airflow channel through the electronic cigarette, leading from one or more air inlets. A downstream end (shown right) of the vaporization chamber 120 connects with a downstream part of the airflow channel, leading to the mouthpiece air outlet. Both ends of the vaporization chamber are open on either side of the heating element 103. Consequently, when a user inhales through the air outlet, air drawn in through the inlet(s) enters the vaporization chamber 120 and follows a longitudinal path, able to flow over both surfaces of the planar heating element 103 before recombining at the far end to travel on to the air outlet. This is shown by the arrows A in the figure. Accordingly, the path length through the vaporization chamber 120 and over the heating element surfaces is relatively long, comprising effectively the full length of the heating element 103. The flowing air is hence able to collect a large amount of vapor, which condenses to form aerosol droplets. Droplets formed at the upstream end of the vaporization chamber have to travel the entire length of the vaporization chamber/heating element, and in the course of this journey may grow to excessive size.

To address this, it is proposed to alter the airflow path to reduce the length of travel through the vaporization chamber, while still maintaining a given heater and vaporization chamber geometry, for example to keep the high level of vapor production achievable from the relatively large heater surface afforded by the planar porous heater configuration. The airflow path is modified to reduce the amount of time that any air molecule travelling on the airflow path spends in a region in which it is able to collect vapor (a region of the vaporization chamber into which vapor is provided by the heater). This time is the dwell time or retention time T, given by T=D/V where D is the air flow path length through a vapor collecting region and V is the air flow velocity along that path. For example, for a given air flow velocity arising from a typical inhalation on the e-cigarette, the dwell time can be reduced by reducing the path length. In various embodiments, the airflow path is configured such that air flows through a shorter or smaller region or volume of the vaporization chamber compared with an unmodified geometry (as in the FIG. 7 arrangement, for example). In some configurations, multiple smaller air flow paths can be provided in different regions of the vaporization chamber so as to access as much of the generated vapor as possible while reducing the dwell time and therefore the droplet size. In either case, the or each portion of the airflow path in which vapor collection occurs occupies a smaller volume of the vaporization chamber than the total vaporization chamber volume.

FIG. 8 shows a simplified cross-sectional view of an atomizer in which the airflow path has been modified, again orthogonal to the heater plane. The airflow A, which is still generally along the longitudinal direction from the upstream end of the atomizer to the downstream end, is diverted so that it passes through the heating element 103, from a first (upper as illustrated) side 103*a* of the heating element 103 to the opposite, second (lower as illustrated) side 103*b* of the heating element 103. The airflow path thus now includes a generally transverse section 40 where it crosses the heating element 103. Preceding and following this transverse part 40 are longitudinal parts 42, 44 of the airflow path.

In addition to the modified airflow path, the proportion of the transit through the vaporization chamber 120 during which the flowing air is able to collect vapor is reduced, as described further below. Thus, the opportunity for excessive aerosol droplet growth is limited, and the maximum droplet size can be kept lower. This is achieved by at least partly restricting the collection of vapor to the part of the airflow including the transverse passage through the heating element, and minimizing vapor collection elsewhere. Accordingly, the transverse section 40 of the airflow path is designated as a vapor collection portion, and the longitudinal sections 42, 44 of the airflow path are designated as transport portions, along which the air flows without significant change in its aerosol fraction (less vapor is collected here than in the vapor collection portion).

To achieve this difference in vapor collection between the different parts of the airflow path, one can introduce physical structures into the atomizer 160 so that air flowing along the transport portions of the path has reduced exposure to vapor in the vaporization chamber 120. The structures act to divert the airflow to create the transverse flow through the heating element 103, and to partition the interior of the atomizer to provide regions distinct from the vaporization chamber 120.

The physical structures may comprise separate components for insertion into an atomizer such as that of the example in FIGS. 2-6, or may be formed integrally with the components of the atomizer, for example as surface features molded on the interior surface of the upper and/or lower cradle components 101, 102.

Accordingly, in embodiments, one or more plenum chambers are provided within the atomizer. Each plenum chamber is separated from the vaporization chamber 120 by a wall or other structure, but lies within the longitudinal extent of the vaporization chamber 120 and/or the heating element 103, transversely spaced from one or other surface 103*a*, 103*b* of the heating element. A plenum chamber receives air entering the atomizer 160 from the upstream side, or delivers air out at the downstream side of the atomizer 160. Also, it communicates with the vaporization chamber 120 to deliver air to or collect aerosol-carrying air from the transverse vapor collection portion 40. The separation of a plenum chamber from the vaporization chamber 120 gives a reduced level of vapor in the plenum chamber so that the aerosol fraction of the air is not significantly altered by passage through the plenum chamber, while the air is still propagated in a generally downstream longitudinal direction to achieve its journey from air inlet to mouthpiece outlet.

FIG. 9 shows a simplified cross-sectional view of an atomizer provided with plenum chambers, to illustrate how the addition of dividing walls within the interior of the atomizer can divert the airflow path to create a transverse portion and also create plenum chambers separated from the vaporization chamber. In this simple example, there are two plenum chambers—a first plenum chamber 122 spaced apart from the first, upper side 103*a* of the heating element 103 through which air travels in a first transport portion 42 of the airflow path through the atomizer 160 and a second plenum chamber 124 spaced apart from the second, lower side 103*b* of the heating element 103 through which air travels in a second transport portion 44 of the airflow path through the atomizer 160. Between the transport portions there is the transverse portion 40 of the airflow path in which air transits the vaporization chamber 120 including passing through the heating element 103, so as to collect vapor generated by the heating element.

The first plenum chamber 122 is bounded by a wall 126 extending in the longitudinal direction from the inlet end of the atomizer 160 to a midpoint along the length of the atomizer 160, the wall being spaced apart in the transverse direction from both the heating element 130 and the upper outer wall of the upper cradle component 101 of the atomizer 160. The region between the upper surface 103 *a* of the heating element 103 and the separating wall 126 can accumulate vapor driven off from the heating element 103 so remains part of the vaporization chamber 120. The region between the separating wall 126 and the inner surface of the outer wall of the upper cradle component 101 is protected from a significant ingress of vapor, and thereby forms the plenum chamber 122 through which air can travel with a reduced collection of vapor. Once air reaches the end of the separating wall 126, it leaves the plenum chamber and enters the vaporization chamber 120 for vapor collection during the vapor collection portion 40 of the path. To direct incoming air to the plenum chamber 122 and prevent it entering the vaporization chamber 120, an end wall 128 closes the upstream end of the atomizer 160 except for an entrance into the plenum chamber 122.

Similarly, the second plenum chamber 124 is bounded by a separating wall 132 extending from a midpoint along the length of the atomizer 160 to the outlet end of the atomizer 160, the wall being spaced apart in the transverse direction from both the heating element 103 and the lower outer wall 102 of the atomizer 160. The region between the lower surface 103 *b* of the heating element 103 and the separating wall 132 forms part of the vaporization chamber 120 while the region between the separating wall 132 and the inner surface of the lower outer wall 102 forms the second plenum chamber 124. After traversing the vapor collection portion 40, air leaves the vaporization chamber 120 and enters the second plenum chamber 124, through which air travels with reduced vapor collection in the second transport portion 44 before exiting the downstream end of the atomizer 160. A second end wall 130 closes the downstream end of the atomizer except for the exit from the second plenum chamber 124, to aid in diverting air leaving the first plenum chamber 122 into the vapor collection portion 40 and second transport portion 44 of the airflow path.

The example of FIG. 9 is particularly simple, and more complex structures can be positioned within the atomizer to form the required airflow path.

FIG. 10 shows a longitudinal cross-sectional view of a further example atomizer 160. This example is configured to take better advantage of the amount of vapor generated by the planar heating element, by causing air to traverse a greater proportion of the vaporization chamber to collect vapor. However, rather than having a single long airflow path through the vaporization chamber as in FIG. 7, with the associated risk of aerosol droplet growth, the FIG. 10 example provides multiple parallel shorter airflow paths through the vaporization chamber. Incoming air is separated into multiple streams, each of which has its own transverse vapor collection portion 40 through a different part of the vaporization chamber 120 and heating element 103, and which are then recombined to exit the atomizer. Thus, long flow paths are avoided while still allowing vapor collection from a substantial longitudinal extent of the heating element 103. A larger amount of aerosol is delivered while avoiding or reducing excess droplet size.

Figure 9:
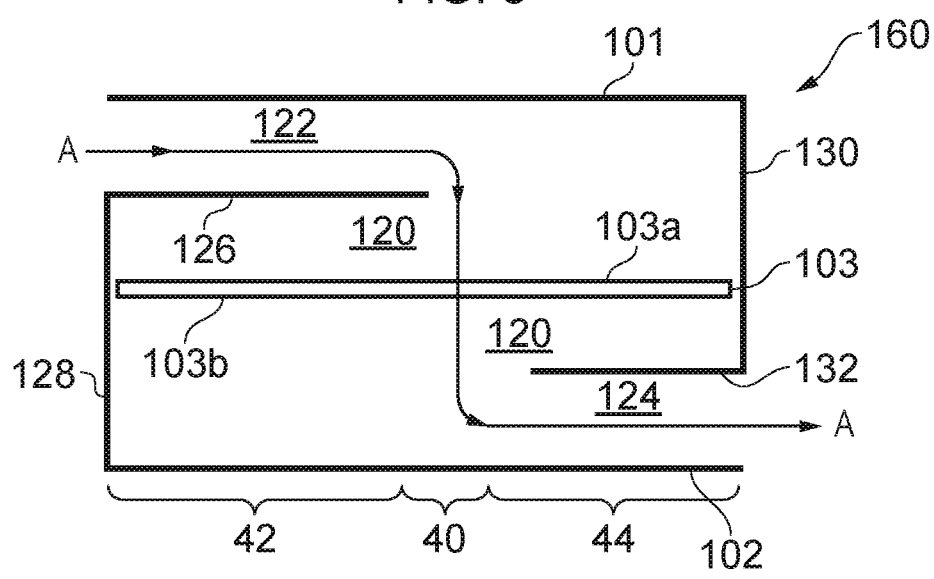
FIG. 9 shows a schematic longitudinal cross-sectional view through a further example atomizer with a modified airflow path including plenum chambers.
Figure 10:
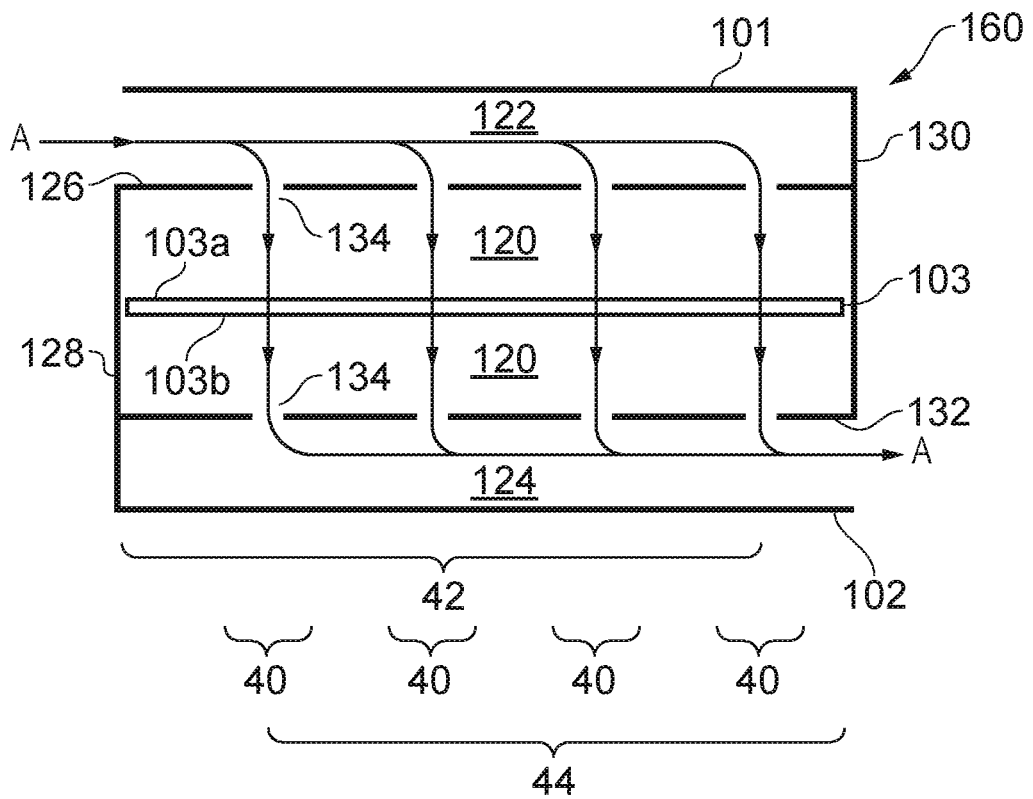
FIG. 10 shows a schematic longitudinal cross-sectional view through a still further example atomizer with a modified airflow path including multiple transverse portions.

The FIG. 10 example differs from the FIG. 9 example in that the two separating walls 126, 132 that divide the plenum chambers 122, 124 from the vaporization chamber 120 extend the full length of the atomizer 160 from the upstream end wall 128 to the downstream end wall 130. In addition, each separating wall 126, 132 has a plurality of apertures 134, spaced apart along the longitudinal dimension. Each aperture 134 in the upper separating wall 126 is an exit from the first plenum chamber 122 into the vaporization chamber 120, and each aperture 134 in the lower separating wall 132 is an entrance into the second plenum chamber 124 from the vaporization chamber 120. Accordingly, incoming air A drawn into the electronic cigarette reaches the atomizer and enters the first plenum chamber 122. A fraction of the air exits the first plenum chamber 122 through the first aperture 134 to enter the vaporization chamber 120, the remaining air continues in the longitudinal direction to the second aperture 134 where a further fraction exits to the vaporization chamber 120, and so on. This example has four apertures 134 in each separating wall, but a different number of apertures may be used as required. The apertures 134 in the upper separating wall 126 act to divide the incoming airflow into four parts, each of which follows a separate transverse vapor collecting path 40 through the heating element 103 from the first side 103a to the second side 103b. Corresponding apertures 134 in the second separating wall 132 allow each fraction of air to leave the vaporization chamber 120 and enter the second plenum chamber 124, where the four parts are recombined into a single air stream to exit the atomizer and progress on to the mouthpiece. Each fraction of the airstream traverses a different length of each plenum chamber, so undergoes a different amount of the first and second transport path 42, 44, although for each fraction the total length of transport path 42, 44 (first plus second) is roughly the same.

Figure 11:
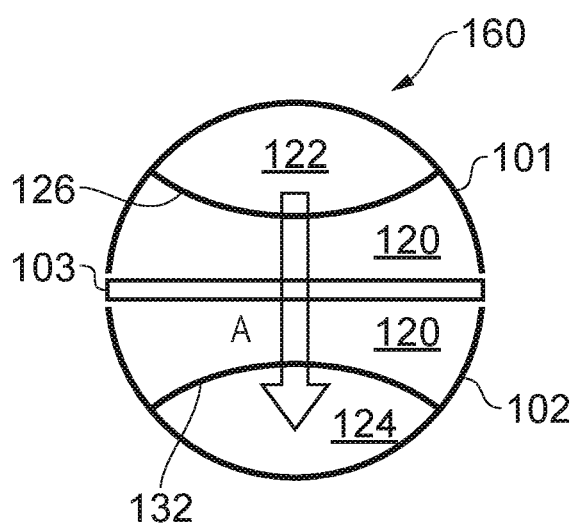
FIG. 11 shows a schematic transverse cross-sectional view through an example atomizer with plenum chambers.

FIG. 11 shows a transverse cross-sectional view of an atomizer configured as the FIG. 9 or FIG. 10 example. This shows the generally circular cross-section of the atomizer 160, and shows that the separating walls 126, 132 may be configured to have a generally arcuate cross-section, curving inwardly opposite to the outward curvature of the outer walls of the upper and lower cradle components 101, 102 of the atomizer 106 to give a generally ovoid cross-section to the plenum chambers 122, 124. The transverse air path A is depicted, flowing from the first plenum chamber 122 through the vaporization chamber 120 to the second plenum chamber 124. This is merely an example, however, and the separating walls 126, 132 may be otherwise shaped (such as flat, for example), as may the outer walls of the upper and lower cradle components 101, 102. The outer walls and separating walls may be integrally formed, such as molding in a single piece.

Alternatively, the separating walls may be formed as plates for insertion into the atomizer, for example by sliding into slots or other receiving and supporting recesses formed in the inner surface of the outer walls of the upper and lower cradle components 101, 102.

Figure 12:
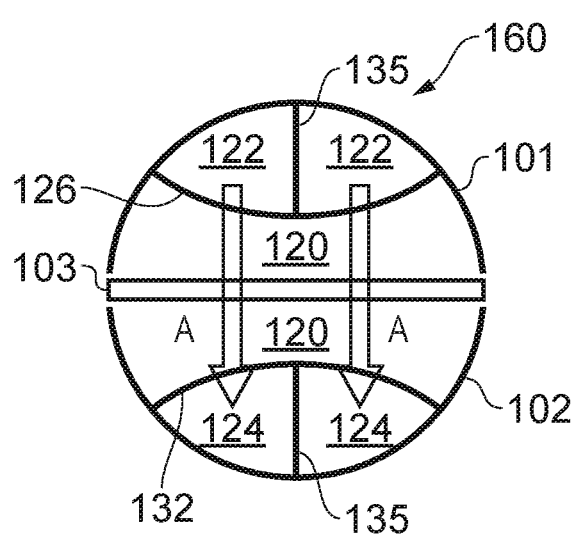
FIG. 12 shows a schematic transverse cross-sectional view through a further example atomizer with plenum chambers.

FIG. 12 shows a transverse cross-sectional view of a further example atomizer. In this example, a further separating wall 135 is provided in each plenum chamber 122, 124 to subdivide the chamber into two smaller plenum chambers, which are adjacent in a direction substantially parallel to the plane of the heating element 103 and orthogonal to the longitudinal direction. Air can enter both plenum chambers, enabling division of the incoming air stream into two halves A spaced in a second dimension orthogonal to the division provided by the longitudinally spaced apertures 134 of the FIG. 10 example. Thus, vapor collection in the vaporization chamber is distributed across the width dimension of the heating element (where "width" merely indicates a direction orthogonal to the longitudinal direction, and does not imply any relative size of these two dimensions of the heating element). Also, further subdivision may be incorporated to produce additional plenum chambers, each of which may have any number of longitudinally spaced apertures connecting to the vaporization chamber. Also, some degree of subdivision may be provided simply by apertures in the separating wall 126, 132 which are spaced apart orthogonal to the longitudinal direction, without the need for the further separating walls 135. Thus the airflow path through the atomizer can be divided into multiple transverse vapor collection paths 40, distributed over the area of the heating element 103 in both the length and width directions to maximize vapor collection.

The examples thus far have relatively simple partitioning by physical structures to separate the plenum chambers from the vaporization chamber and form the desired airflow path. To some extent, there will be a reliance on the pressure difference along the overall air channel through the electronic cigarette when a user inhales to pull air along the required direction. The vaporization chamber is largely an open volume, and in some cases air may not take the shortest route through the heating element from the first plenum chamber to the second plenum chamber. Some lateral travel may occur (in a plane roughly parallel to the heating element), giving a longer dwell time in the vaporization chamber and the chance that the aerosol droplets will increase to an undesired size.

Accordingly, other examples may include physical structures that provide further guidance for the flowing air to maintain the flow more closely along the desired path(s), and/or partitioning of the vaporization chamber to limit lateral movement of the air. The structures may take the form of baffles, vanes, walls, fins, blades, recesses, cavities, or other configurations.

Figure 13:
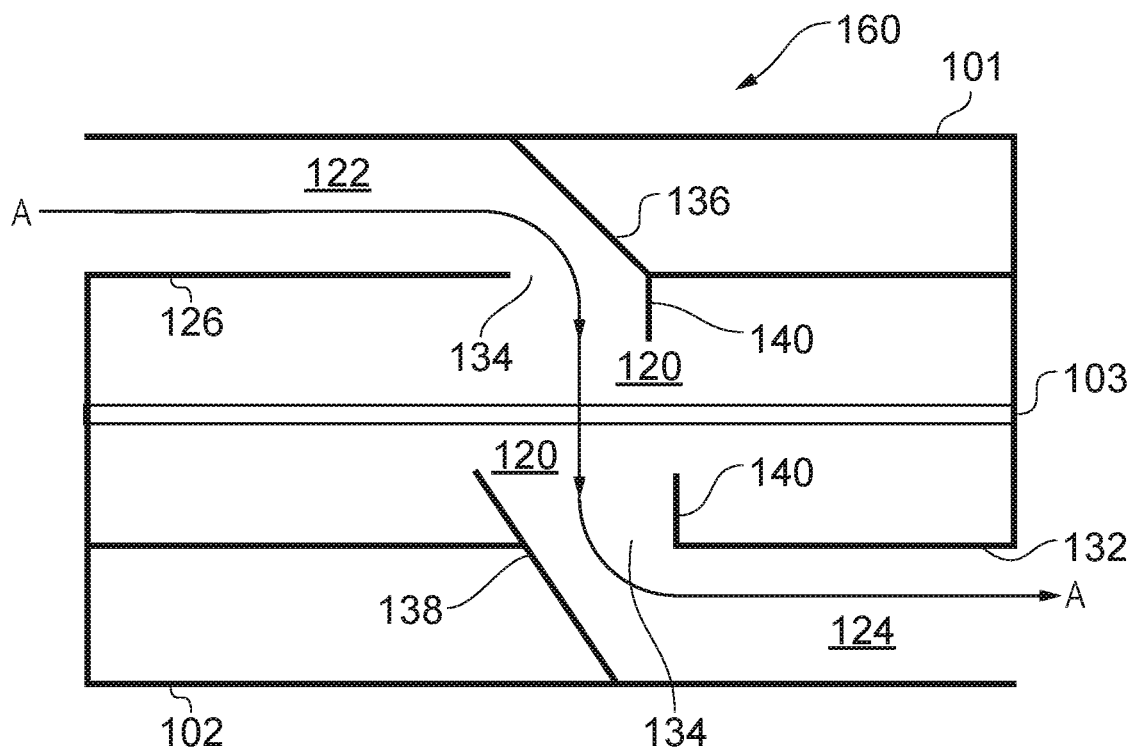
FIG. 13 shows a schematic longitudinal cross-sectional view through an example atomizer with having plenum chambers and partition walls.

FIG. 13 shows a longitudinal cross-sectional view of an example atomizer configured in this way. In this example, which shows a single aperture 134 in each plenum chamber wall 126, 132 for simplicity, a sloped wall 136 closes the first plenum chamber 122 after the aperture 134. This directs all air into the vaporization chamber and stops air gathering in the closed downstream end of the first plenum chamber 122. Similarly, a sloped wall 138 closes the second plenum chamber 124 upstream of the aperture 134, to stop air entering the upstream end of the second plenum chamber and to direct air towards the air outlet at the downstream end. The sloping of these walls provides some aerodynamicism, giving a smoother airflow. Additionally, baffles 140 are provided at the edges of the apertures 134, protruding slightly into the vaporization chamber. These inhibit lateral movement of the air to ensure that more air makes the desired journey from first plenum chamber 122 to second plenum chamber 124 via the transverse path through the vaporization chamber 120.

Figure 14:
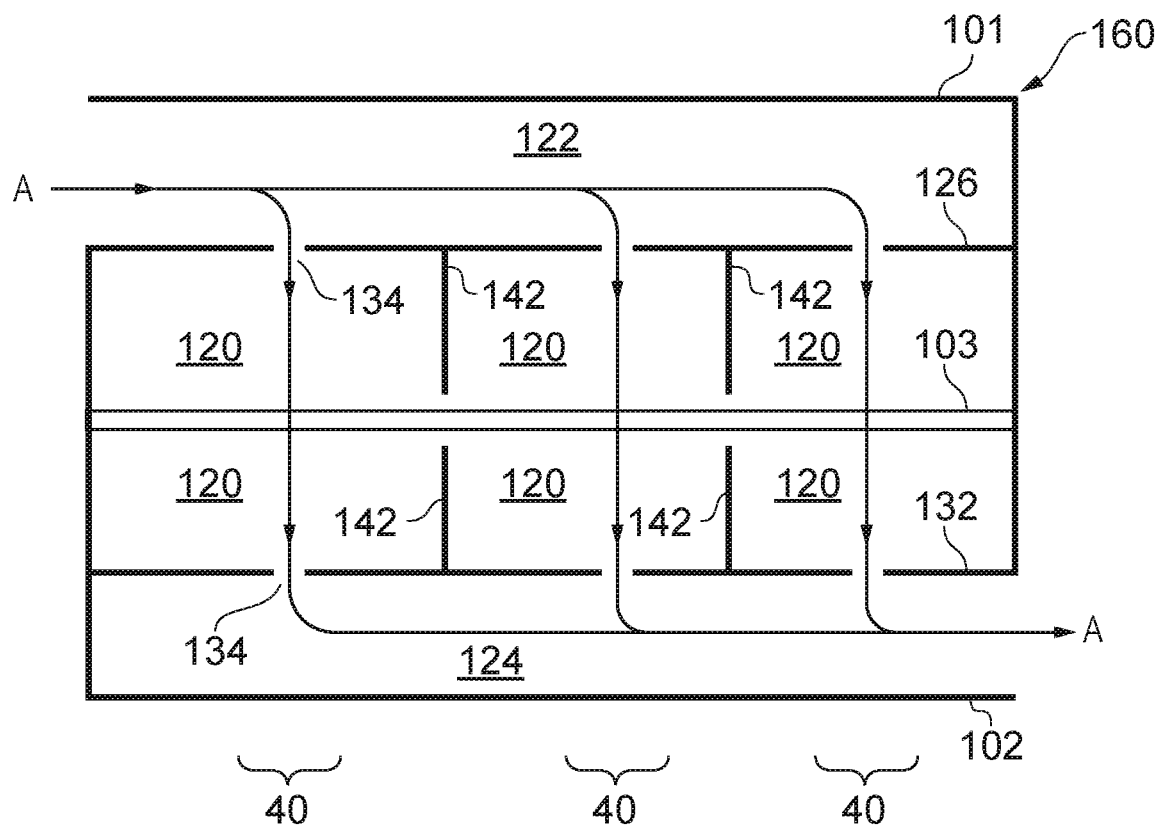
FIG. 14 shows a schematic longitudinal cross-sectional view through an example atomizer with having plenum chambers and multiple partition walls.

FIG. 14 shows a longitudinal cross-sectional view of an example atomizer configured with a partitioned vaporization chamber. The separating walls 126, 132 that form the plenum chambers 122, 124 in this example each have three apertures 134 connecting with the vaporization chamber 120. Additionally, a partition wall 142 extends from the separating walls 126, 132 between each pair of adjacent apertures 134, into the vaporization chamber 120 to subdivide the vaporization chamber into separate regions, one for each of the transverse vapor collecting paths 40. Each partition wall 134 in this example reaches close to the heating element 103 but does not touch it. This can reduce heating of the partition walls 142 by direct thermal transfer from the heating element 103. In other examples it may be acceptable for the partition walls to contact the heating element 103, to provide isolation of the vaporization chamber regions from one another. Alternatively or additionally, partition walls 142 might extend into the vaporization chamber from side or end walls of the atomizer, rather than from the separating walls 126, 132. For transverse paths spaced across the width of the heating element, there may be partition walls spaced in this dimension. The partition walls 142 may be integrally formed with the various other walls such as by molding, or may be fabricated separately and assembled later. For example, the partitioning walls may be connected at their edges or at intersections into a single element defining a plurality of separate cells, one for each transverse path, which is simply placed above and below the heating element when assembling the components of an atomizer such as that of the FIGS. 2 to 6 example. Alternatively, the partitioning walls may protrude from a plate forming the separating wall, giving a single element for insertion into an upper or lower part of the vaporization chamber.

FIG. 15 shows a transverse cross-section of an atomizer 106 having partition walls 142 which are spaced across the width of the heating element 103.

FIG. 16A shows a perspective view of a first example insert partitioning element 144 for dividing the vaporization chamber either above or below the heating element, and providing ten regions for the vaporization chamber. The walls 142 of the insert 144 are connected at their intersections. FIG. 16B shows a perspective view of a second example insert partitioning element 144, providing three regions and with walls 142 connected around the perimeter of the insert. Clearly, the shapes and relative positions of the walls 142 may differ from these examples, to fit with the configuration of other parts of an atomizer. As mentioned, the partitioning walls 142 may be supported on a plate forming a separating wall 126, 132 for defining a plenum chamber; such a plate is indicated in phantom in FIG. 16A. The partitioning walls may be thought of as fins or vanes extending from the surface of the plate forming the separating wall, where the plate may be flat or non-flat, such as curved, arched or otherwise concave or convex.

The above examples are not to be considered as limiting. Many other configurations of physical structure to divide the plenum chambers from the vaporization chamber, to partition the vaporization chamber, to guide the air along the desired flow path, to smooth the airflow, and to close potential "dead ends" will be readily apparent to the skilled person, and are considered to be within the scope of the present disclosure.

As noted above, a vapor generating element such as the planar heating element of the FIG. 2 to FIG. 6 device comprises a porous sheet-like material. Accordingly, air is able to pass through the vapor generating element via its pores to traverse the transverse vapor collecting portion of the airflow path through the atomizer. The individual pore size, the density of the pores (porosity) and the thickness of the vapor generating element are factors which will dictate how easy it is for air to be drawn through the heating element, and hence how hard the user has to inhale on the electronic cigarette. This required inhalation strength is known as "resistance to draw". In some cases, it may be that the structure of the porous sheet produces a resistance to draw which is considered too high; a user will need to inhale with inconvenient force to draw air through the electronic cigarette. Therefore, in some examples it is proposed that the vapor generating element be provided with one or more openings (through holes from one side of the sheet to the other) in addition to the pores.

These openings, of which one or more may be provided, will have at least one dimension in the plane of the sheet heating element which is greater than the largest width of pores in the porous sheet material. Alternatively, the opening size can be selected so that a cross-sectional area of the or each opening is greater than a largest cross-sectional area of the pores in the porous sheet material. Alternatively, it may be more convenient to define that a dimension or cross-sectional area of an opening is larger than an average width or average cross-sectional area of the pores in the porous sheet material. For example, the opening size (dimension or cross-sectional area) may be specified as at least two times, at least three times, at least five times, at least ten times, at least 20 times, at least 50 times, or at least 100 times greater than a largest or average pore width or pore cross-sectional area. This ratio of larger opening(s) to smaller pores allows air to pass more easily through the heating element while preserving the wicking properties of the porous structure of the heating element.

Also, one can consider the total cross-sectional area of the openings. To allow comfortable puffing when inhaling on the electronic cigarette and to give a relatively low pressure drop across the heating element, it is proposed that the total cross-sectional area of all openings in the heating element is at least 0.5 mm$^2$. This is the area of the openings as offered to the transversely flowing air crossing the heating element.

Returning to the example atomizer of FIGS. 2 to 6, the heating element 103 is provided with slots extending inwardly from the two longer edges. While these slots are used for aligning the heating element 103 in the cradle components 101, 102 by use of the teeth 110, and also to create a serpentine current path to produce a range of temperatures from the element when heated, it is proposed that they may also be used as openings for the easier passage of air through the heating element.

As an example, it is noted above that the FIG. 2 atomizer may have a longitudinal dimension of around 20 mm, and a width of around 8 mm. The slots may extend inwardly by around 4.8 mm and have a width of around 0.6 mm. Hence the total cross-sectional area of the six slots is 6×4.8 mm×0.6 mm=17.28 mm$^2$, comfortably in excess of the above-proposed lower limit of 0.5 mm$^2$ (even when allowing for some of the slot area being closed by the supporting walls of the cradle components).

Figure 17:
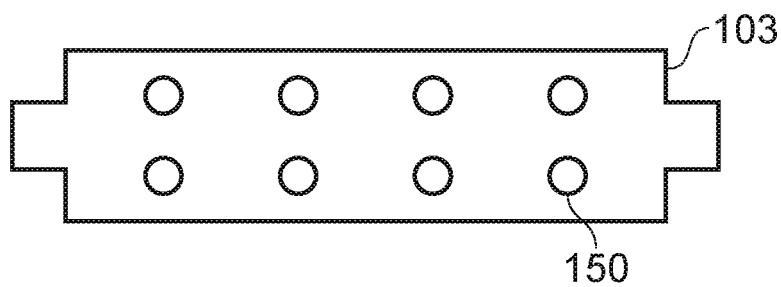
Figure 18:
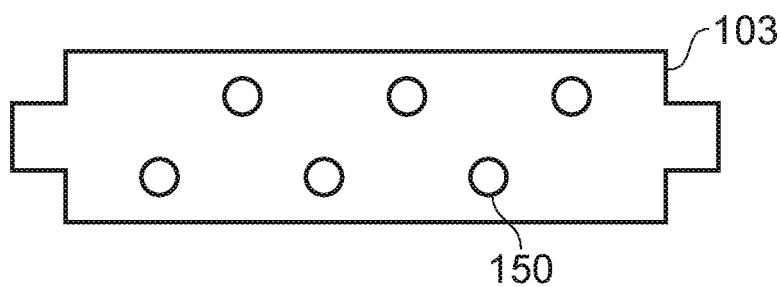
Figure 19:
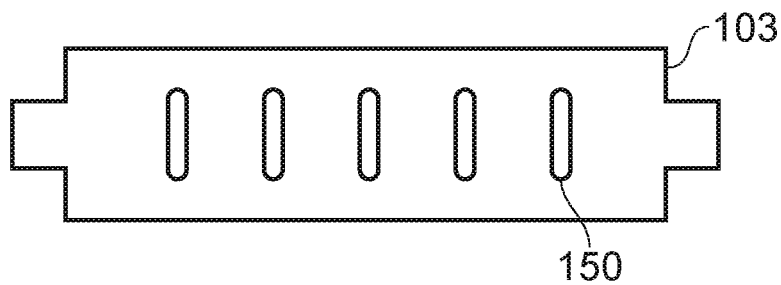

Other sizes, shapes, positions and quantities of openings may be used as desired. FIG. 17 shows a plan view of example heating element having eight openings 150 of roughly circular shape arranged in two rows along the length of the heating element 103. The openings 150 may be aligned across the rows as in FIG. 17, or may be staggered along the two rows, as shown in FIG. 18. The openings need not be circular; other shapes may be used. More than two rows, or a single row, may also be used. For example, FIG. 19 shows a plan view of a heating element 103 having slot-shaped openings 150 in a single row along the centre of heating element. These various arrangements of openings will divert the current path to a serpentine shape as in the FIG. 2 slotted example, although in each case the path will be different. The openings can be chosen to both tailor the current path and the resulting heating profile across the heating element, and give a desired number of parallel transverse air paths and a desired resistance to draw.

In an atomizer provided with both partitioning walls (such as the FIGS. 13-16 examples) and openings in the heating element, the partitioning walls may be arranged so as to partition the vaporization chamber with reference to the openings, for example by providing one vaporization chamber region per opening.

Figure 20:
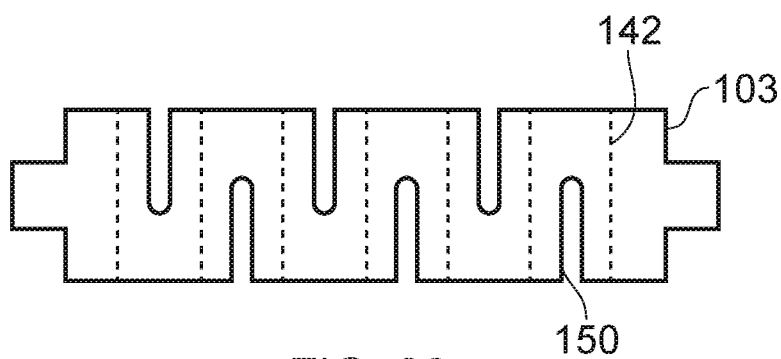

FIG. 20 show a plan view of a slotted heating element 103 such as in the FIG. 2 example, with dotted lines to show a possible location of partitioning walls 142. The vaporization chamber is thereby divided into six regions, each coinciding with one of the slots 150. The separating walls forming the plenum chambers may be provided with apertures aligned with each region/opening to deliver air to and from the vaporization chamber regions for travel along each of the vapor collecting portions of the airflow path. Air will pass through the curved inner ends of the slots 150, since the outer ends are blocked by the alignment teeth and supporting edges of the cradle walls when the heating element is installed in an atomizer cradle.

FIG. 21 shows a plan view of a further example slotted heating element 103 as in the FIG. 2 example, with solid lines showing the location of partitioning walls 142. Each wall is set at an angle to extend across the heating element 103 from the base of one slot 150 to the base of an adjacent slot 150, reaching to the edge of vaporization chamber as indicated by the dashed lines which show where the heating element passes through the walls of the vaporization chamber to reach into the reservoir. In this way, each section of the vaporization chamber, corresponding to an individual slot, is isolated from the other sections so that air cannot flow from one to another. The shape and configuration of the walls 142 is such as to direct air leaving the upper plenum chamber via an aperture or apertures 134 in the upper separating wall aligned with a slot 150 to flow through that slot (represented by the converging arrows on the left of the Figure). Once through the slot, the air flow can diverge, to be collected by one or more apertures 134 in the lower separating wall also aligned with the slot so as to enter the lower plenum chamber (represented by the diverging arrows on the right of the Figure). Although airflow is depicted for only two slots, in reality, the air will converge and diverge via every slot, with air delivery and collection to the vapor collecting portions corresponding to each slot enabled by apertures in the separating walls for each plenum chamber. Note the shape of the apertures 134, two of which only are indicated in the Figure by dotted lines. Each aperture has an arcuate profile reflecting and following the curved end of its corresponding slot 150, but not overlapping with the slot. In other words, the aperture edge is offset from the slot end in the general direction of the airflow along the airflow path from and to the plenum chambers. In the upper separating wall, the aperture edge is offset in the upstream airflow direction and in the lower separating wall the aperture edge is offset in the downstream airflow direction. In this way, the air can take a sloping path along the vapor collection portion, being generally directed across a part of the heater so that it has the opportunity to collect more vapor as compared to a vertical path straight through the slot which might arise if the apertures and slots were overlapping. At other edges, including along the partitioning walls 142 and the edge of the vaporization chamber (dashed line), the apertures follow these edges. Other shapes of aperture may be used if preferred. The aperture edges may be inwardly spaced from the walls, for example, and the curved edge may be differently shaped to correspond with a differently shaped slot end.

The examples discussed above have suggested the use of one or more plenum chambers both above and below the vapor generating element. However, the proposed modified airflow path can be supported at least to some extent with a plenum chamber or chambers provided on only one side of the vapor generating element. Hence, an atomizer may comprise a single plenum chamber either above or below the vapor generating element, one plenum chamber on each side of the vapor generating element, or at least two plenum chambers on one side in conjunction with no, one or more plenum chambers on the other side. A different number of plenum chambers might be provided on each side of the vapor generating element. For example, a plurality of plenum chambers on the upstream side of the atomizer may act to divide the incoming airflow into multiple transverse airflows to cross the vapor generating element, while a single plenum chamber on the downstream side can collect and recombine these multiple airflows to output from the atomizer.

The examples above have suggested an upstream plenum chamber to be above the heating element and a downstream plenum chamber to be below the heating element, but the opposite arrangement can be used, and the concept of "above" and "below" loses context in an assembled electronic cigarette which can be held at any angular rotation by the user. Hence, the more general terms "first side of the vapor generating element" and "second side of the vapor generating element" are more relevant, where the two sides are opposite to each other. The upstream, inlet end of the atomizer and the downstream, outlet side of the atomizer are arranged to communicate with opposite sides of the vapor generating element, and either may be associated with the first side or the second side. Similarly, the vapor generating element, being planar, has a first surface on its first side and a second, opposite, surface on its second side.

Planar porous vapor generating elements such as heating elements suitable for use in atomizer according to examples of the present disclosure may be formed by stamping or cutting (such as laser cutting) the required shape from a larger sheet of porous material. This may include stamping out, cutting away or otherwise removing material to create openings as described above.

Heating elements may, for example, be made from a conductive material which is a nonwoven sintered porous web structure comprising metal fibers, such as fibers of stainless steel. For example, the stainless steel may be AISI (American Iron and Steel Institute) 316 L (corresponding to European standard 1.4404). The material's weight may be in the range of 100-300 g/m2. Its porosity may be greater than 50%, or greater than 70%, where porosity is the volume of air per volume of the material, with a corresponding density less than 50% or less than 30%, where density is the volume of fibers per volume of the material. Thickness of the material may be in the range of 75-250 µm. A typical fiber diameter may be about 12 µm, and a typical mean pore size (size of the voids between the fibers) may be about 32 µm. An example of a material of this type is Bekipor® ST porous metal fiber media manufactured by NV Bekaert SA, Belgium, being a range of porous nonwoven fiber matrix materials made by sintering stainless steel fibers.

The present disclosure is not limited to heating elements made from such material, and is applicable widely to heating elements made from planar porous conductive materials, including porous ceramic material. Also, materials suitable for generating vapor by vibration may also be used as required, depending on the operating regime of the vapor generating element. Note also that while the material is described as planar, this refers to the relative dimensions of the sheet material and the heating elements (a thickness many times smaller than the length and/or width) but does not necessarily indicate flatness, in particular of the final heating element made from the material. A heating element may be flat but might alternatively be formed from sheet material into a non-flat shape such as curved, rippled, corrugated, ridged, or otherwise made concave and/or convex. Also, embodiments may be implemented with vapor generating elements that are not planar, but rather are cylindrical (such as molded from ceramic) or configured as an elongate coil. A sufficiently open structure or apertures may be included to allow transverse air flow for the vapor collecting portion, or air flow might not pass through the heating element. Also, more than one vapor generating element may be included, for example arranged in an array so that each element provides vapor to a different part of the volume of the vaporization chamber.

The examples above have been largely confined to arrangements in which the vapor collecting portions of the airflow path are transverse, and pass through the vapor pour generation element, and the transport portions of the airflow path are longitudinal, in that they are substantially parallel to but spaced apart from the plane of the heating element. However, neither of these conditions is required, and a reduced dwell time for vapor collection can be implemented without either one or both of these airflow configurations.

FIG. 22 shows a longitudinal cross-sectional view of a further example atomizer 160, in which at least a part of the airflow path through the plenum chambers (the transport portion(s)) is not longitudinal with respect to the plane of the heater 103. The example is similar to the atomizer of FIG. 10, but the plenum chambers 122 and 124 are additionally shaped by interior walls that form funnel shapes. A longitudinal part of the upper plenum chamber 122 connects to the necks of two funnels 200 so that air A in the plenum chamber can enter one or other funnel, and flow along the neck in a direction substantially orthogonal to the longitudinal direction, towards the heater 103. The funnel necks lead to funnel mouths, formed by sloping walls extending to the separating wall 126, in which a number of apertures 134 are defined as before. Each funnel mouth encompasses three apertures 134 (in this example) so that air travelling in one plenum funnel 200 is divided into three parts for travel through the vaporization chamber 120 and the heater 103. Hence each funnel feeds three vapor collecting portions. On the second side of the heater 103, the second separating wall 132 has corresponding set of apertures 134 to collect air from the vapor collecting portions, and allow it to travel, still in an orthogonal direction, into the mouths of a second pair of funnels 200 in the second plenum chamber 124, oppositely arranged to the funnels in the first plenum chamber 122. The second funnels 200 converge to funnel necks which discharge air into a common passage of the second plenum chamber 124 in which air flows longitudinally to exit the atomizer 160. Hence, in this example, a proportion of the air flow in the plenum chambers (the transport portions of the airflow path through the atomizer) follows a non-longitudinal direction. It will be appreciated that the plenum chambers may readily be shaped and configured in a variety of different arrangements that give airflow paths in direction other than longitudinal for the transport portions, while still delivering air to and collecting it from the vapor collection portion(s). Hence, the disclosure is not limited with regard to the direction of airflow in the transport portions, relative to the orientation of components of the atomizer.

Figure 23:
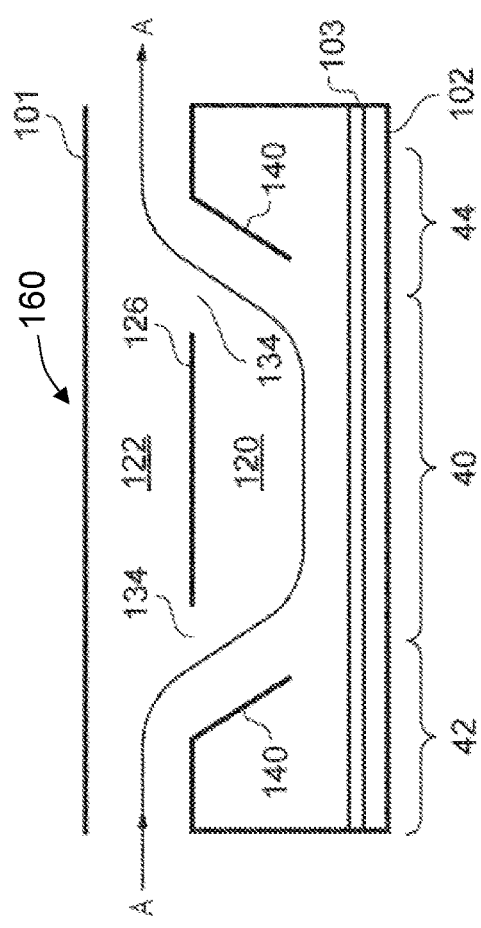
FIG. 23 is a schematic longitudinal cross-sectional view through an example atomizer configured for non-transverse airflow in a vapor collecting portion of the airflow path.

FIG. 23 shows a longitudinal cross-sectional view of a further example atomizer 160, in which the airflow path in the vapor collecting portion does not pass through the vapor generating element. In this example, the vaporization chamber 120 is largely defined on the first side of the heater 103 only, and a single plenum chamber 122 is provided also on the first side of the heater 103. The separating wall 126 has a first and second aperture 134, so that air A entering the atomizer 160 flows along the plenum chamber in a first transport portion 42, exits a first aperture 134 to enter the vaporization chamber 120, travels through the vaporization chamber 120 in a vapor collecting portion 40, and is drawn back into the plenum chamber 122 through a second aperture 134 to flow along a second transport portion 44 in the plenum chamber 122 until it leaves the atomizer. In this way, air is retained on an upper side of the heating element 103 only, and does not flow through it. Baffles 140 extend from the borders of the apertures 134 into the vaporization chamber 120 to aid in directing the airflow along the intended path. This format of plenum chamber could be mirrored on the second side of the heating element 103 to provide a second airflow path. It will be appreciated again that the plenum chambers may be shaped and configured in other ways that provide airflow through the atomizer in which the vapor collecting portion does not comprises transverse airflow through the heating element.

Hence, in various examples, the airflow in the vapor collection portion may be transverse through the heating element, may remain on one side of the heating element, or may flow past or around the heating element to move from one side to another (airflow around a coil, for example).

It is also contemplated that the user may be able to adjust the aerosol provision of an atomizer by modifying the vapor collection portion of the airflow path (which may correspondingly modify the transport portion or portions also). If the vapor collection portion is altered so as to change the dwell time, the amount of vapor collected and/or the size of aerosol droplet which is able to form can be adjusted according to user preference. This can be achieved by, for example, enabling reconfiguration of the vapor collecting portion to change the airflow path length and correspondingly change the dwell time. Alternatively, a change in the bore of the airflow path, such as the size of apertures in the separating wall leading from the plenum chamber to the vaporization chamber, could change the velocity of the air as it enters the vapor collecting portion, again giving a change to the dwell time. One or more movable or otherwise adjustable components or elements can be provided to achieve this control.

Figure 24:
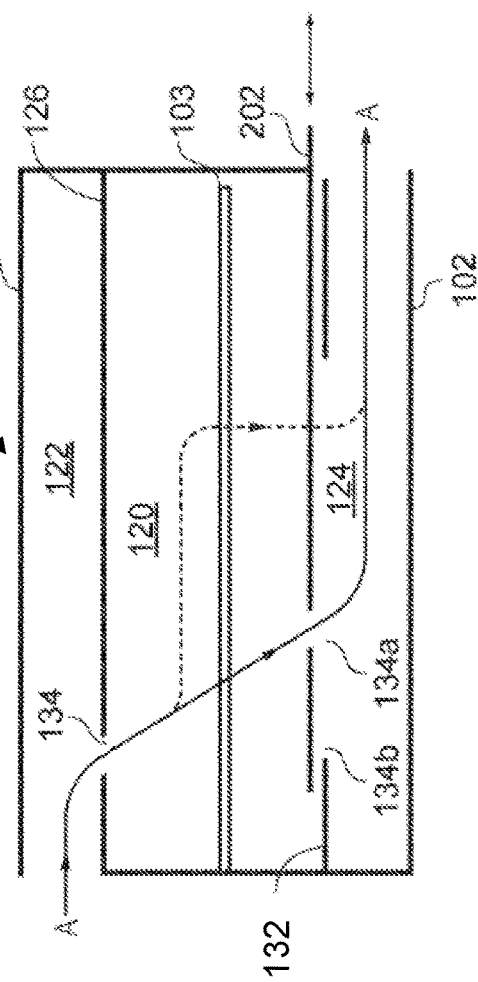
FIG. 24 is a schematic longitudinal cross-sectional view through an example atomizer configured for control of air dwell time in the vapor collection portion of the airflow path.

FIG. 24 shows a longitudinal cross-sectional view of a simple example atomizer 160 configured to provide adjustment of aerosol droplet size. An upper plenum chamber 122 with a single aperture 134 in its separating wall 126 leading into the vaporization chamber 120 is provided, and paired with a lower plenum chamber 124 also having a single aperture 134a, to collect air from the vaporization chamber 120 after it has travelled the vapor collecting portion. However, the aperture 134a, of a similar size to the aperture 134 in the upper separating wall 126, is located in a sliding plate 202, slidable along the longitudinal direction over the surface of the separating wall 132 that forms the lower plenum chamber 124. The separating wall 132 has a further aperture 134b which has a greater longitudinal extent than the aperture 134a in the sliding plate 202, so that when the plate is moved and the position of the aperture 134a changes, the aperture still opens from the vaporization chamber 120 into the lower plenum chamber 124. In this way, the aperture 134a can be moved from an upstream position close to the first aperture 134 from the upper plenum chamber 122, so that the vapor collecting portion has a relatively short path length, to a downstream position remote from the first aperture 134 so that the vapor collecting portion has a longer path length. Intermediate positions can be used to select an intermediate path length. Accordingly, the vapor collection portion path length can be altered, to give a corresponding adjustment in dwell time and hence in aerosol droplet size. The sliding plate 202 can be mechanically coupled to a user control (mechanical or electrical) on the exterior of the electronic cigarette to enable a user to adjust its position.

In a similar way, a sliding plate might be provided which slides over the aperture 134 in the upper separating wall 126 to partially cover or uncover the aperture so that the aperture size can be changed, with the aim of changing the airflow velocity along the vapor collection portion to change the dwell time.

Alternative implementations for changing the dwell time by allowing user adjustment of the path length and/or the airflow velocity will be apparent. A variety of movable elements may be employed to reconfigure the airflow path through the atomizer may be envisaged.

In any example, the separating walls, any partitioning walls and any other baffles, vanes, fins, blades, cavities and the like can be considered as physical structures disposed in the vaporization chamber which act to divert, modify and/or divide the airflow path to reduce the dwell time of air in the vaporization chamber compared to the same chamber without those physical structures.

In general, an airflow path through an atomizer has at least one portion which is separated from the vaporization chamber by one or more structures (walls and the like) defining one or more plenum chambers so as to reduce the dwell time in the vaporization chamber of air flowing through the atomizer. In the absence of said structures, the dwell time for the vaporization chamber would be longer, allowing aerosol droplets to grow to a larger size. Hence, the structures, which confine part of the airflow path to the plenum chambers, act to reduce or control droplet size.

Experimental results have been obtained which demonstrate the reduction in droplet (particle) size that can be obtained by using a transverse air flow arrangement through a planar porous heater.

Figure 25:
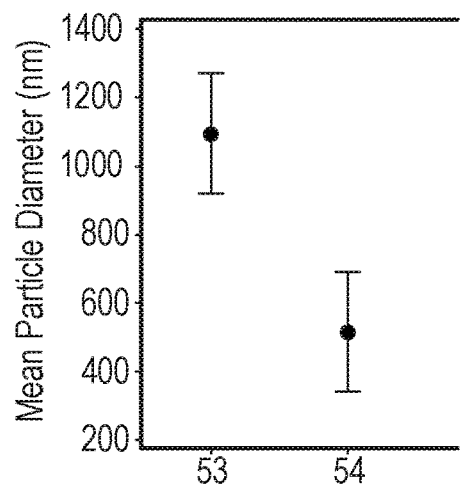
FIG. 25 is a graph showing mean droplet diameters measured for test atomizers with parallel and transverse air flow paths.

FIG. 25 shows a plot of data measured from two air flow configurations. For each configuration, a mean droplet (particle) diameter was measured. The data point 53 is the particle diameter obtained using a planar porous heater of the type shown in FIGS. 2 to 5, configured for air flow substantially parallel to the heater surface and over the full length of the heater, similar to the arrangement shown in FIG. 7. The mean measured diameter was 1096.7 nm. In contrast, the data point 54 is the particle diameter obtained using a substantially identical planar porous heater, configured for operation in the same way as the "53" arrangement except that the air flow was arranged to follow the transverse direction, passing through the heater. The mean measured diameter was 516.7 nm. Hence, an air flow pathway that is configured with a reduced vapor collection portion, in this case by passing the air flow through a porous planar heater instead of over its surface, can reduce the droplet size to less than half.

Figure 26:
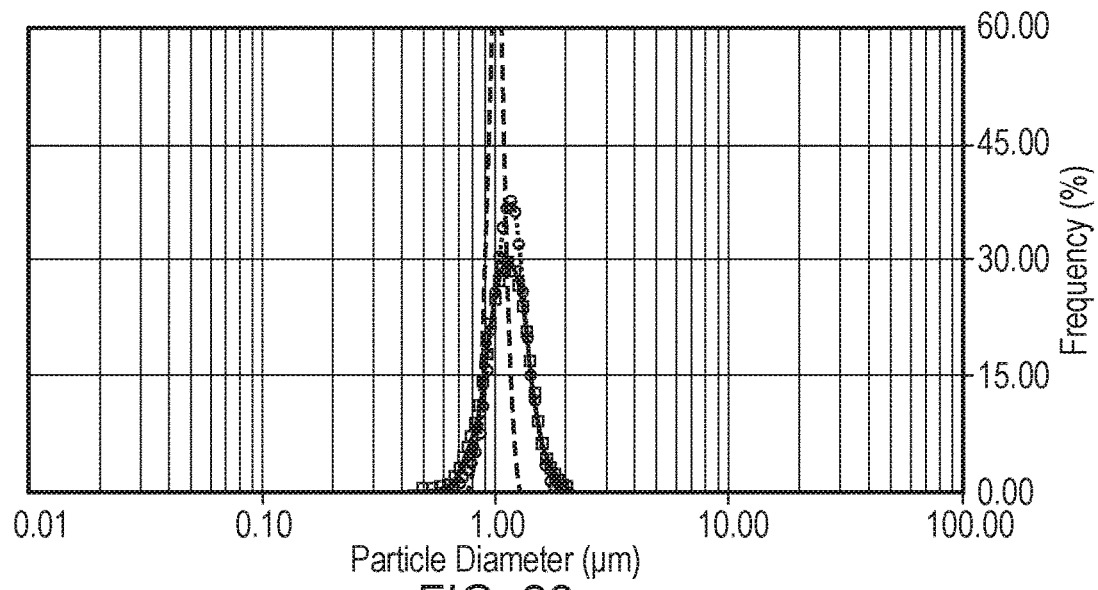
FIG. 26 is a graph of frequency of droplet diameter measured over three uses of a test atomizer with a parallel air flow path.

FIG. 26 shows graphs of the frequency of occurrence of particle diameter measured for the "53" parallel air flow arrangement for each of three operational tests. This data gives the 1096.7 nm mean value noted above, and shows a fair consistency of droplet size across multiple operations of the apparatus.

Figure 27:
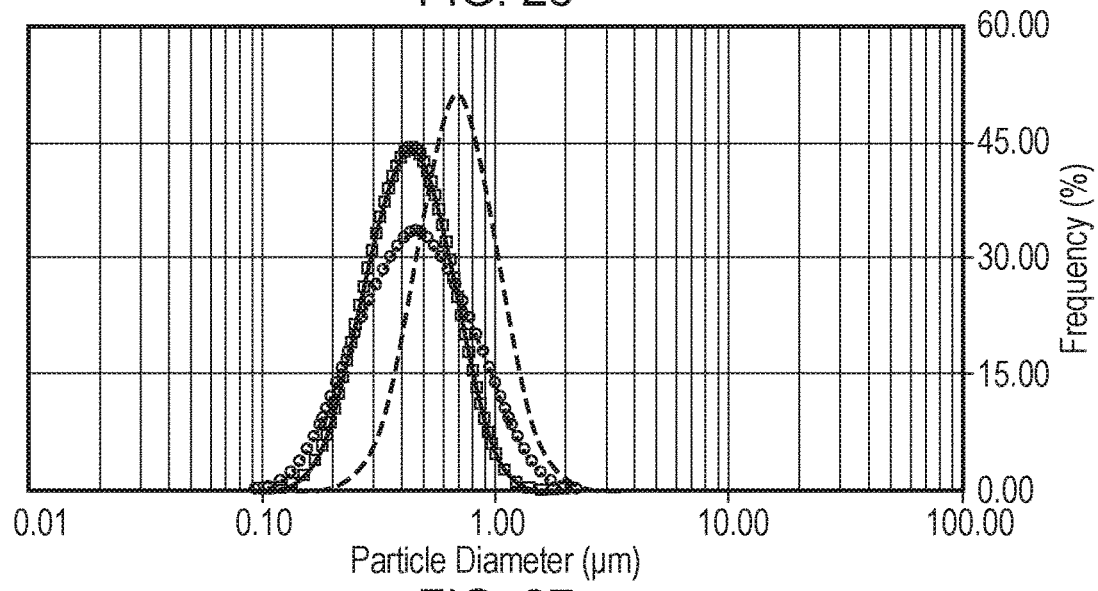
FIG. 27 is a graph of frequency of droplet diameter measured over three uses of a test atomizer with a transverse air flow path.

FIG. 27 shows three corresponding graphs of particle diameter measured for the "54" transverse airflow arrangements. This data gives the 516.7 nm mean value noted above, and also shows consistency of droplet size across multiple operations of the apparatus. Hence, the observed approximately 50% decrease in droplet size achieved from a transverse air flow is considered to be a real and repeatable effect.

In addition to the reduced dwell time discussed above, the smaller droplet size from a transverse air flow may arise from any or all of several other effects. Flow through a planar porous heater reduces opportunities for droplet (particle) coagulation and hence the formation of larger droplets. Also, flow through the porous structure of the heater produces a drag force on forming droplets in a direction normal to the heater surface. Smaller droplets will experience less drag, allowing them to be entrained more easily into the airflow than larger droplets. Any larger droplets that do form may impact physical structures provided to direct the transverse air flow (walls of the plenum chambers, for example) and thereby be removed from the air flow.

An atomizer in accordance with the above examples may be included as part of an aerosol producing component (reusable or disposable), such as a cartomizer or clearomizer, for detachable coupling to a battery section to form an electronic cigarette or other vapor provision device (electronic or non-electronic), or may be incorporated directly into an electronic cigarette or other vapor provision device (electronic or non-electronic) that does not comprise detachable or separable components.

The various embodiments described herein are presented only to assist in understanding and teaching the claimed features. These embodiments are provided as a representative sample of embodiments only, and are not exhaustive and/or exclusive. It is to be understood that advantages, embodiments, examples, functions, features, structures, and/or other aspects described herein are not to be considered limitations on the scope of the invention as defined by the claims or limitations on equivalents to the claims, and that other embodiments may be utilized and modifications may be made without departing from the scope of the claimed invention. Various embodiments of the invention may suitably comprise, consist of, or consist essentially of, appropriate combinations of the disclosed elements, components, features, parts, steps, means, etc., other than those specifically described herein. In addition, this disclosure may include other inventions not presently claimed, but which may be claimed in future.

The invention claimed is:

1. An atomizer for a vapor provision system comprising:
a vaporization chamber having a volume;
a vapor generating element disposed in the vaporization chamber for providing vapor into the volume of the vaporization chamber;
at least one plenum chamber separated from the vaporization chamber; and
an air flow path through the atomizer comprising:
a vapor collecting portion through the vaporization chamber being smaller than the volume of the vaporization chamber, along which air travels to collect vapor provided by the vapor generating element; and
at least one transport portion through a plenum chamber, the at least one transport portion delivering air to or collecting air from the vapor collecting portion, wherein:
the vapor generating element is planar and comprises a longitudinally extending porous sheet having a first surface and an opposite second surface; and
the vapor collecting portion is arranged such that air travels transversely through the vapor generating element from the first surface to the second surface.

2. The atomizer according to claim 1, wherein:
the at least one plenum chamber is transversely spaced from the vapor generating element with respect to a longitudinal extent to the vapor generating element; and
the at least one transport portion is arranged such that air travels longitudinally through a plenum chamber.

3. The atomizer according to claim 1, comprising at least two transport portions comprising a first transport portion through a plenum chamber transversely spaced from the first surface of the vapor generating element to deliver air to the vapor collecting portion and a second transport portion through a plenum chamber transversely spaced from the second surface of the vapor generating element to collect air from the vapor collecting portion.

4. The atomizer according to claim 1, wherein the air flow path comprises one or more additional vapor collecting portions through different regions of the vaporization chamber.

5. The atomizer according to claim 4, wherein the vapor collecting portions together occupy substantially the whole of the volume of the vaporization chamber.

6. The atomizer according to claim 4, wherein each vapor collecting portion passes through a different part of the vapor generating element.

7. The atomizer according to claim 4, further comprising at least one partition wall dividing the vaporization chamber into two or more regions, each region corresponding to a vapor collecting portion of the airflow path.

8. The atomizer according to claim 7, wherein the at least one partition wall extends into the vaporization chamber from a separating wall that separates the at least one plenum chamber from the vaporization chamber.

9. The atomizer according to claim 1, further comprising one or more separating walls to separate the at least one plenum chamber from the vaporization chamber.

10. The atomizer according to claim 9, wherein the at least one separating wall includes one or more apertures, each communicating with the vapor collecting portion of the airflow path.

11. The atomizer according to claim 9, wherein the one or more separating walls comprise a plate for insertion into the atomizer to effect separation of an associated plenum chamber from the vaporization chamber.

12. The atomizer according to claim 1, wherein the vapor generating element includes at least one opening through which air can travel in the at least one vapor collecting portion of the air flow path to pass from the first surface to the second surface.

13. The atomizer according to claim 12, wherein the at least one opening comprises a plurality of slots extending inwardly from edges of the vapor generating element.

14. The atomizer according to claim 13, wherein the slots extend perpendicularly inwards from longitudinally extending edges of the vapor generating element.

15. The atomizer according to claim 12, wherein the at least one opening has a larger cross-sectional area than a largest cross-sectional area of pores in the porous sheet.

16. The atomizer according to claim 12, wherein a cross-sectional area of the at least one opening is greater than or equal to $0.5 \text{ mm}^2$.

17. The atomizer according to claim 1, wherein the vapor generating element is a heating element configured to generate vapor by heating, and the porous sheet is an electrically conductive porous sheet formed from a woven or non-woven web of metal fibers.

18. The atomizer according to claim 1, further comprising one or more movable elements configured to be moved by a user to alter a dwell time of air travelling in the vapor collecting portion, so as to control an aerosol droplet size of vapor collected by air in the vapor collecting portion.

19. The atomizer according to claim 18, wherein the one or more movable elements are configured to alter at least one of the volume airflow path length of the vapor collecting portion, or an airflow velocity in the vapor collecting portion.

20. A vapor provision system comprising the atomizer according to claim 1.

21. An atomizer for a vapor provision system comprising:

a vaporization chamber;

a planar vapor generating element disposed in the vaporization chamber and comprising a longitudinally extending porous sheet having a first surface and an opposite second surface;

at least one plenum chamber separated from the vaporization chamber and transversely spaced from a surface of the vapor generating element; and an air flow path through the atomizer comprising:

a vapor collecting portion through the vaporization chamber in which air travels transversely through the vapor generating element from the first surface to the second surface; and at least one transport portion through a plenum chamber in which air travels longitudinally, the at least one transport portion delivering air to or collecting air from the vapor collecting portion.

22. An atomizer for a vapor provision system comprising:

a vaporization chamber having a volume;

a vapor generating element disposed in the vaporization chamber for providing vapor into the volume of the vaporization chamber;

at least one plenum chamber separated from the vaporization chamber; and an air flow path through the atomizer comprising:

a vapor collecting portion through the vaporization chamber being smaller than the volume of the vaporization chamber, along which air travels to collect vapor provided by the vapor generating element; and at least one transport portion through a plenum chamber, the at least one transport portion delivering air to or collecting air from the vapor collecting portion, wherein:

the at least one plenum chamber is transversely spaced from the vapor generating element with respect to a longitudinal extent to the vapor generating element; and the at least one transport portion is arranged such that air travels longitudinally through a plenum chamber.

* * * * *